United States Patent
Gemma

(10) Patent No.: US 11,826,193 B2
(45) Date of Patent: Nov. 28, 2023

(54) CONTROL DEVICE AND CONTROL PROGRAM

(71) Applicant: FUJIFILM CORPORATION, Tokyo (JP)

(72) Inventor: Kohei Gemma, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 180 days.

(21) Appl. No.: 17/488,334

(22) Filed: Sep. 29, 2021

(65) Prior Publication Data

US 2022/0096042 A1 Mar. 31, 2022

(30) Foreign Application Priority Data

Sep. 30, 2020 (JP) ................................ 2020-166472

(51) Int. Cl.
*A61B 6/00* (2006.01)
*A61B 6/04* (2006.01)

(52) U.S. Cl.
CPC ............ *A61B 6/547* (2013.01); *A61B 6/0414* (2013.01); *A61B 6/461* (2013.01); *A61B 6/502* (2013.01)

(58) Field of Classification Search
CPC ................................ A61B 6/502; A61B 6/461
See application file for complete search history.

(56) References Cited

U.S. PATENT DOCUMENTS

| | | |
|---|---|---|
| 2016/0151032 A1 | 6/2016 | Muller et al. |
| 2017/0172531 A1 | 6/2017 | Sugiyama et al. |
| 2020/0337662 A1* | 10/2020 | Nakayama ........... A61B 8/5269 |
| 2021/0030373 A1* | 2/2021 | Arai ...................... G06T 11/005 |

FOREIGN PATENT DOCUMENTS

| | | |
|---|---|---|
| JP | H11-196397 A | 7/1999 |
| JP | 2008-036279 A | 2/2008 |
| JP | 2008-086389 A | 4/2008 |
| JP | 2011-031799 A | 2/2011 |
| JP | 2013-172900 A | 9/2013 |
| JP | 2017-113540 A | 6/2017 |
| WO | 2020069031 A1 | 4/2020 |

OTHER PUBLICATIONS

English language translation of the following: Office action dated Jun. 13, 2023 from the JPO in a Japanese patent application No. 2020-166472 corresponding to the instant patent application. This office action translation is submitted now in order to supplement the understanding of the cited references which are being disclosed in the instant Information Disclosure Statement.

* cited by examiner

*Primary Examiner* — Dani Fox
(74) *Attorney, Agent, or Firm* — SOLARIS Intellectual Property Group, PLLC

(57) ABSTRACT

A control device including: at least one processor, wherein the processor is configured to acquire inclination information indicating an inclination of an imaging surface of an imaging table in a mammography apparatus that irradiates a breast in a compressed state between the imaging surface of the imaging table and a compression member with radiation from a radiation source to capture a radiographic image and perform control to adjust information, which is displayed on a projection surface of the compression member by projection of a projection image by an image projection unit, according to the inclination indicated by the inclination information.

15 Claims, 15 Drawing Sheets

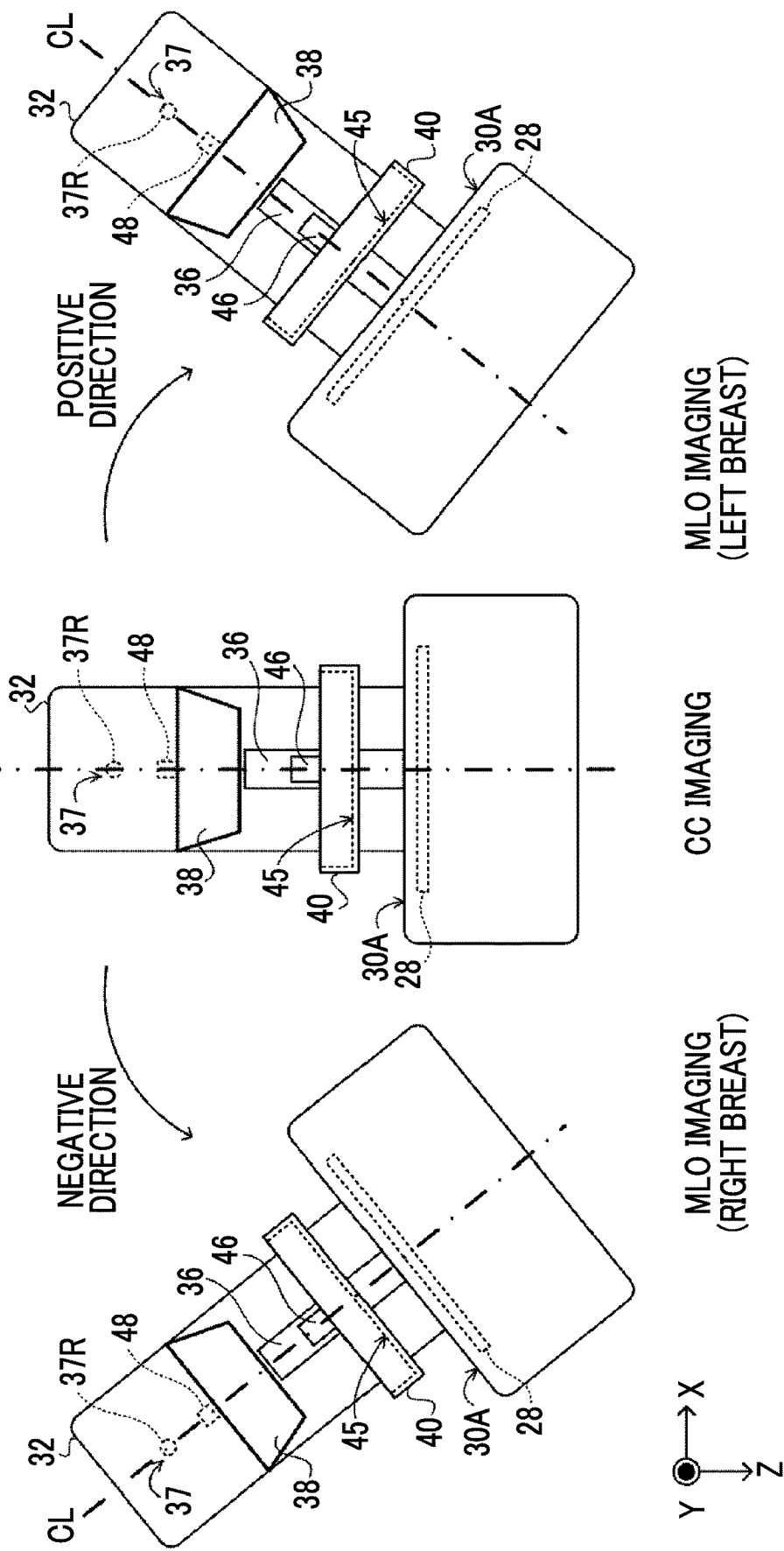

CONTROL DEVICE AND CONTROL PROGRAM

CROSS-REFERENCE TO RELATED APPLICATION

The present application claims priority under 35 U.S.C. § 119 to Japanese Patent Application No. 2020-166472 filed on Sep. 30, 2020. The above application is hereby expressly incorporated by reference, in its entirety, into the present application.

BACKGROUND

Technical Field

The present disclosure relates to a control device and a non-transitory computer-readable storage medium storing a control program.

Description of the Related Art

A mammography apparatus is known which irradiates a breast compressed by a compression member with radiation to capture a radiographic image. In a case in which imaging is performed, information or the like for assisting the imaging may be displayed. For example, JP2008-086389A discloses a technique that displays a skin line of a breast on a liquid crystal display (LCD) and displays a projection image thereof on a projection surface of a compression member.

However, in some cases, a radiographic image of the breast is captured in a state in which an imaging surface of an imaging table is inclined. In this case, a user, such as a radiology technician, positions the breast on the inclined imaging surface of the imaging table and compresses the breast with a compression member.

In a case in which the breast is positioned on the inclined imaging surface of the imaging table in this way, the user stands at a position corresponding to the inclination of the imaging surface of the imaging table and performs the positioning. Therefore, it is difficult to see information displayed by a projection image, which may impose a burden on the user.

The present disclosure has been made in view of the above-mentioned problems, and an object of the present disclosure is to provide a control device and a non-transitory computer-readable storage medium storing a control program that can reduce a burden on a user who positions a breast.

SUMMARY

In order to achieve the above object, according to a first aspect of the present disclosure, there is provided a control device comprising at least one processor. The processor is configured to acquire inclination information indicating an inclination of an imaging surface of an imaging table in a mammography apparatus that irradiates a breast in a compressed state between the imaging surface of the imaging table and a compression member with radiation from a radiation source to capture a radiographic image and performs control to adjust information, which is displayed on a projection surface of the compression member by projection of a projection image by an image projection unit, according to the inclination indicated by the inclination information.

According to a second aspect of the present disclosure, in the control device according to the first aspect, the processor may perform control to adjust a direction in which the information is displayed to a direction corresponding to the inclination.

According to a third aspect of the present disclosure, in the control device according to the first aspect, the processor may perform control to switch the direction, in which the information is displayed, between a case in which the imaging surface of the imaging table is inclined with respect to the subject pertaining to the breast and a case in which the imaging surface is not inclined with respect to the subject.

According to a fourth aspect of the present disclosure, in the control device according to the first aspect, the processor may not perform the control regardless of the inclination in a case in which the information is information indicating at least one of a shape or a position of the breast.

According to a fifth aspect of the present disclosure, in the control device according to the first aspect, in a case in which the information includes character information, the processor may perform control to adjust a display position of the character information to a position corresponding to the inclination.

According to a sixth aspect of the present disclosure, in the control device according to the first aspect, in a case in which a size of an irradiation field of the radiation emitted from the radiation source is smaller than a size of the projection surface and the information is character information, the processor may perform control to adjust a display position of the character information to a position outside the irradiation field.

According to a seventh aspect of the present disclosure, in the control device according to the fifth aspect, the character information may include characters indicating at least one of a compression pressure of the compression member against the breast in past imaging and current imaging, a thickness of the compressed breast, or information indicating a degree of the inclination.

According to an eighth aspect of the present disclosure, in the control device according to the first aspects, in a case in which a size of an irradiation field of the radiation emitted from the radiation source is smaller than a size of the projection surface and the information is information indicating at least one of a shape or a position of the breast in the compressed state, the processor may perform control to adjust a display position of the information to a position inside the irradiation field.

According to a ninth aspect of the present disclosure, in the control device according to the first aspect, in a case in which a size of an irradiation field of the radiation emitted from the radiation source is equal to or larger than a size of the projection surface, the processor may perform control to adjust a display position of the information to the same position regardless of the inclination.

In addition, in order to achieve the above object, according to a tenth aspect of the present disclosure, there is provided a control device comprising at least one processor. The processor is configured to perform control such that a direction of information displayed on a projection surface of a compression member by a projection image projected by an image projection unit is different between a case in which a mammography apparatus performs CC imaging in which a radiation source and an imaging table are disposed in a cranio-caudal direction of a subject and a radiographic image of a breast of the subject compressed by the compression member is captured and a case in which the mammography apparatus performs MLO imaging in which the radiation source and the imaging table are inclined with respect to the subject and a radiographic image of the breast compressed by the compression member is captured.

According to an eleventh aspect of the present disclosure, in the control device according to the tenth aspect, the processor may perform the control on character information including at least one of a compression pressure of the compression member against the breast in past imaging and current imaging, a thickness of the compressed breast, or information indicating a degree of inclination of the radiation source and the imaging table with respect to the subject and may perform control such that information indicating a shape of the breast is displayed in the same direction in a case in which the CC imaging is performed and in a case in which the MLO imaging is performed.

Further, in order to achieve the above object, according to a twelfth aspect of the present disclosure, there is provided a control device comprising at least one processor. The processor is configured to control an image projection unit which projects a projection image onto a projection surface of a compression member in a mammography apparatus that irradiates a breast compressed by the compression member with radiation from a radiation source to capture a radiographic image such that, in a case in which a size of an irradiation field of the radiation emitted from the radiation source is equal to or larger than a size of an image displayed on the projection surface by the projection image, character information including characters indicating at least one of a compression pressure of the compression member against the breast in past imaging and current imaging, a thickness of the compressed breast, or information indicating a degree of inclination of a support portion that supports the radiation source with respect to a subject pertaining to the breast is displayed inside the irradiation field and that, in a case in which the size of the irradiation field is smaller than the size of the image displayed on the projection surface by the projection image, the character information is displayed outside the irradiation field.

Furthermore, in order to achieve the above object, according a thirteenth aspect of the present disclosure, there is provided a non-transitory computer-readable storage medium storing a control program that causes a computer to perform a process comprising: acquiring inclination information indicating an inclination of an imaging surface of an imaging table in a mammography apparatus that irradiates a breast in a compressed state between the imaging surface of the imaging table and a compression member with radiation from a radiation source to capture a radiographic image; and performing control to adjust information, which is displayed on a projection surface of the compression member by projection of a projection image by an image projection unit, according to the inclination indicated by the inclination information.

Moreover, in order to achieve the above object, according to a fourteenth aspect of the present disclosure, there is provided a non-transitory computer-readable storage medium storing a control program that causes a computer to perform a process comprising: performing control such that a direction of information displayed on a projection surface of a compression member by a projection image projected by an image projection unit is different between a case in which a mammography apparatus performs CC imaging in which a radiation source and an imaging table are disposed in a cranio-caudal direction of a subject and a radiographic image of a breast of the subject compressed by the compression member is captured and a case in which the mammography apparatus performs MLO imaging in which the radiation source and the imaging table are inclined with respect to the subject and a radiographic image of the breast compressed by the compression member is captured.

In addition, in order to achieve the above object, according to a fifteenth aspect of the present disclosure, there is provided a non-transitory computer-readable storage medium storing a control program that causes a computer to perform a process comprising: controlling an image projection unit which projects a projection image onto a projection surface of a compression member in a mammography apparatus that irradiates a breast compressed by the compression member with radiation from a radiation source to capture a radiographic image such that, in a case in which a size of an irradiation field of the radiation emitted from the radiation source is equal to or larger than a size of an image displayed on the projection surface by the projection image, character information including characters indicating at least one of a compression pressure of the compression member against the breast in past imaging and current imaging, a thickness of the compressed breast, or information indicating a degree of inclination of a support portion that supports the radiation source with respect to a subject pertaining to the breast is displayed inside the irradiation field and that, in a case in which the size of the irradiation field is smaller than the size of the image displayed on the projection surface by the projection image, the character information is displayed outside the irradiation field.

According to the present disclosure, it is possible to reduce the burden on the user who positions the breast.

BRIEF DESCRIPTION OF THE DRAWINGS

Exemplary embodiments according to the technique of the present disclosure will be described in detail based on the following figures, wherein:

FIG. 2B is a diagram illustrating the inclination of an imaging surface of an imaging table in CC imaging and MLO imaging.

DETAILED DESCRIPTION

Hereinafter, embodiments of the present disclosure will be described in detail with reference to the drawings. In addition, each of the embodiments does not limit the present disclosure.

First Embodiment

Figure 1:
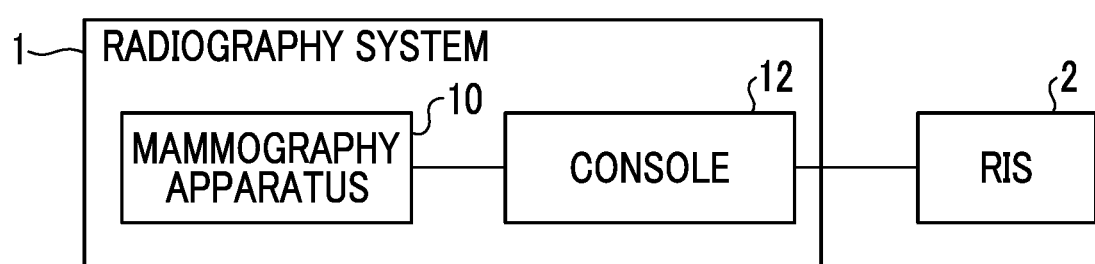
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of a control device according to the present disclosure.

Figure 2A:
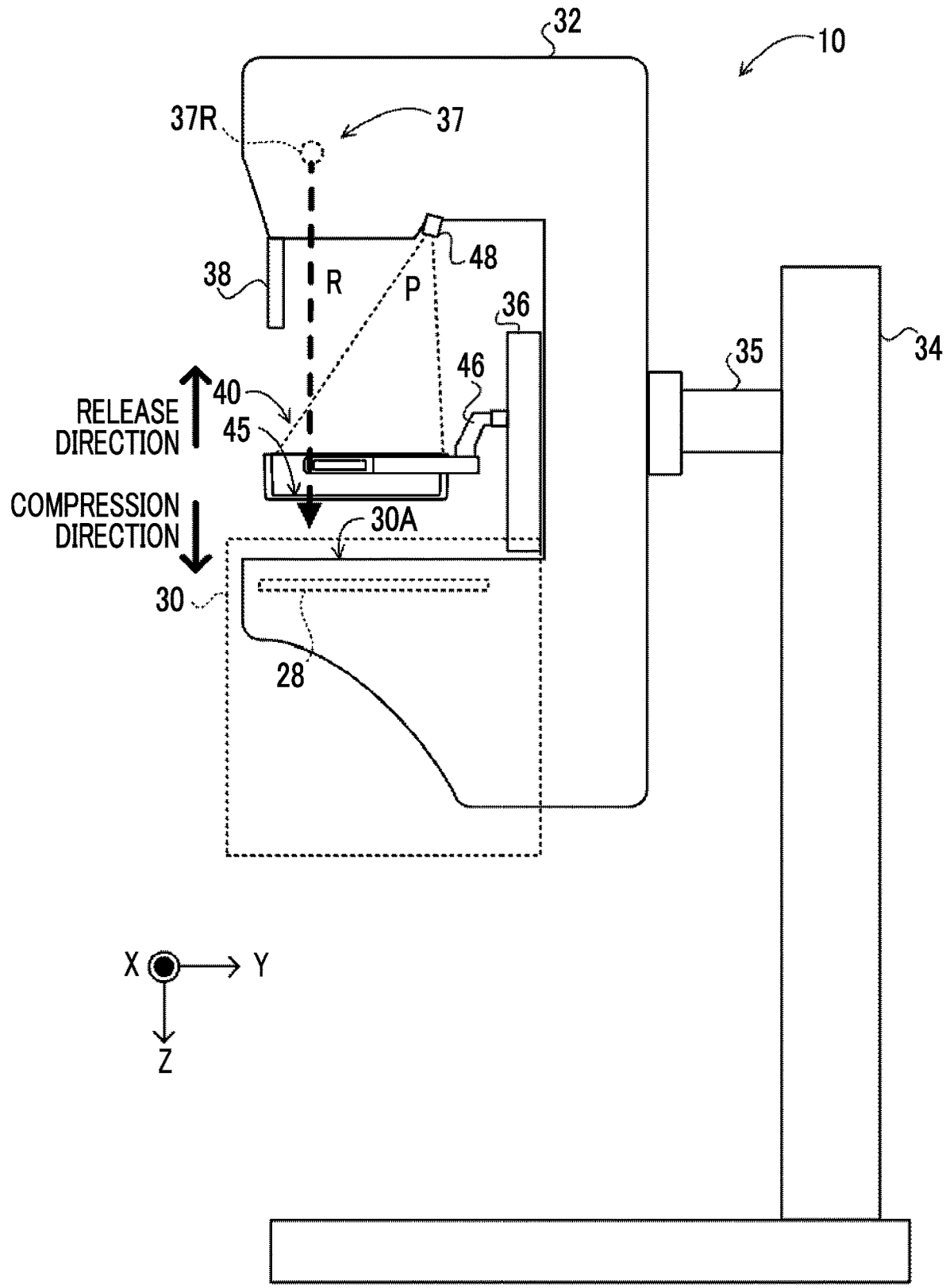
FIG. 2A is a side view illustrating an example of the outward appearance of a mammography apparatus according to the embodiment.
Figure 3:
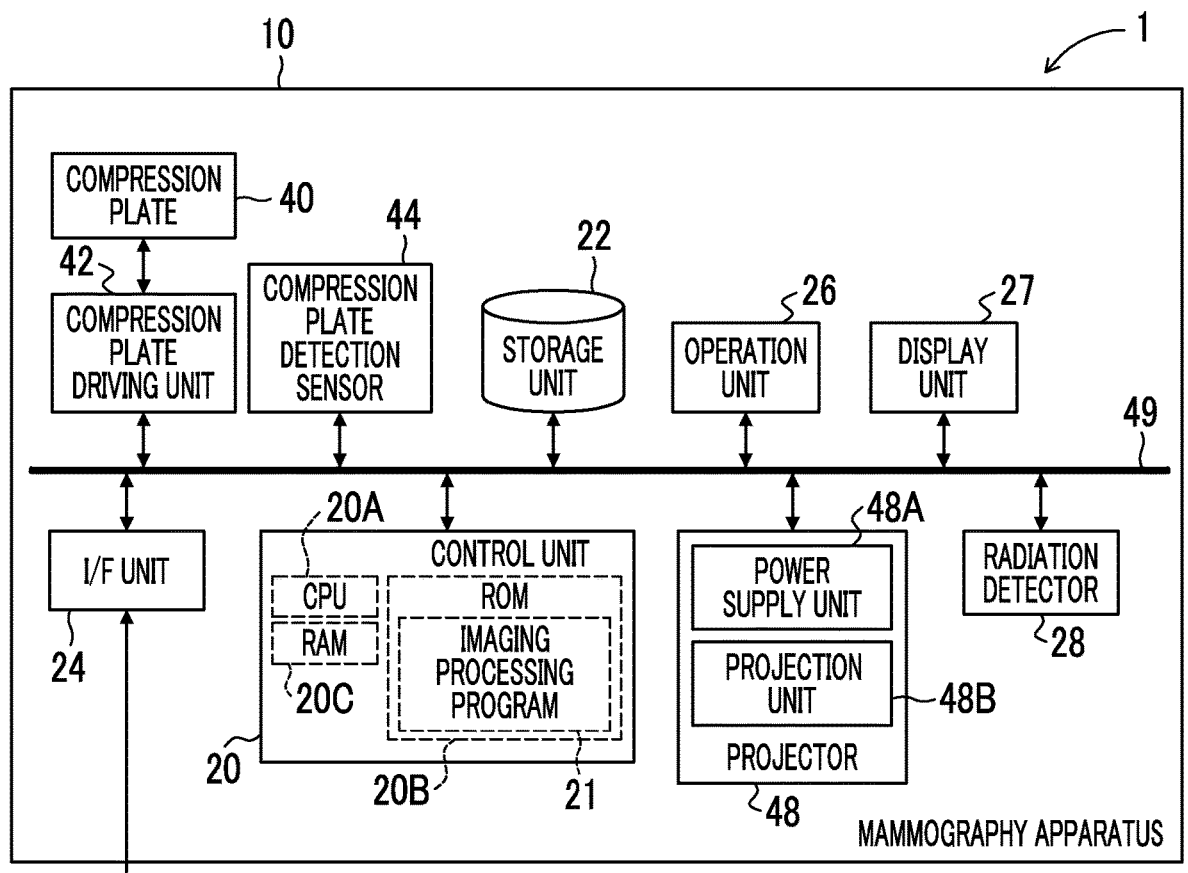
FIG. 3 is a block diagram illustrating an example of the configuration of the mammography apparatus and a console according to the embodiment.
Figure 3:
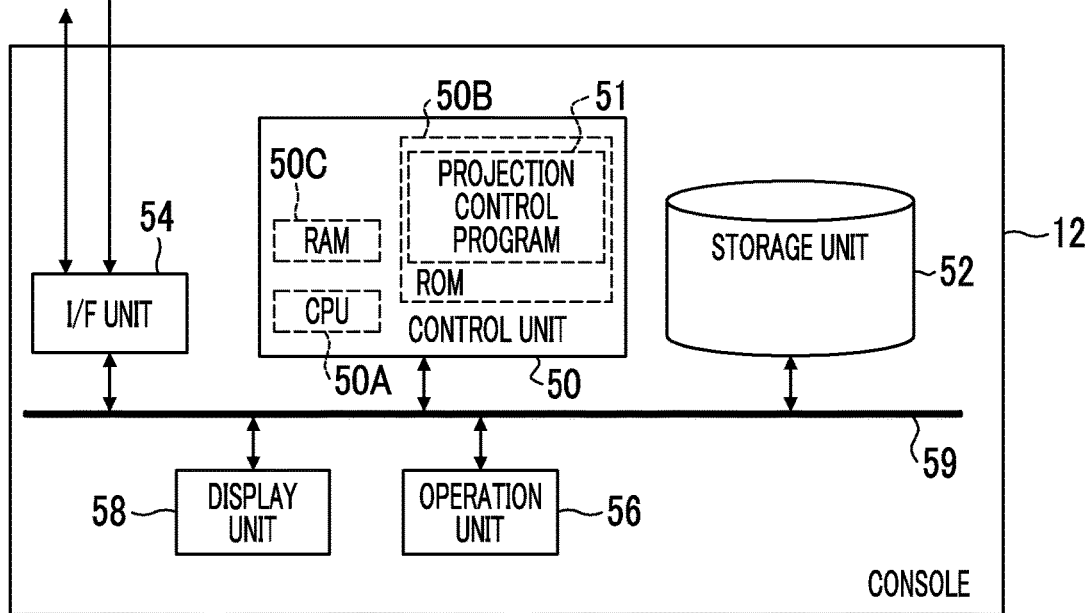

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 3 is a functional block diagram illustrating an example of the configuration of the mammography apparatus 10 and the console 12 according to this embodiment.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting, for example, on a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. The face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and medio-lateral oblique (MLO) imaging in which the imaging direction is a medio-lateral oblique direction for the breast.

FIG. 2B illustrates an example of the state of the imaging table 30, the arm portion 32, and the radiation source 37R in the CC imaging and the MLO imaging. As illustrated in FIG. 2B, in a case in which the CC imaging is performed, the imaging surface 30A is adjusted to face the upper side (the head of the subject) of the mammography apparatus 10 in a state in which it faces the radiation source 37R. Therefore, the radiation R is emitted from the radiation source 37R to the breast in a direction from the head to the foot of the subject, and the CC imaging is performed.

On the other hand, as illustrated in FIG. 2B, in a case in which the MLO imaging is performed, the arm portion 32 is rotated up to a predetermined angle within the range of, for example, 45 degrees or more and less than 90 degrees in a negative direction or a positive direction with respect to the case in which the CC imaging is performed so as to be inclined with respect to the cranio-caudal direction. Specifically, in a case in which the left breast is imaged, the arm portion 32 is inclined in the positive direction, with the imaging surface 30A and the radiation source 37R facing each other, such that the imaging surface 30A is inclined to the right. In a case in which the right breast is imaged, the arm portion 32 is inclined in the negative direction, with the imaging surface 30A and the radiation source 37R facing each other, such that the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 3) that moves a compression plate 40 compressing the breast in the up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit to compress the breast of the subject between the compression plate 40 and the imaging table 30. The reason why the breast is compressed by the compression plate 40 is, for example, to expand the overlap of the mammary gland tissues to make it easy to determine whether the mammary gland tissue is a benign lesion or a malignant lesion, to suppress the blurring of a radiographic image to make it easy to see a mammary gland structure or the like, to fix the breast to suppress the body movement of the subject, and to decrease the thickness of the breast to reduce the radiation exposure of the breast. As illustrated in FIG. 2A, for the movement direction of the compression plate 40, the direction in which the breast is compressed, that is, the direction in which the compression plate 40 becomes closer to the imaging surface 30A is referred to as a "compression direction", and the direction in which the compression of the breast is released, that is, the direction in which the compression plate 40 becomes closer to the radiation emitting unit 37 is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression plate detection sensor (see a compression plate detection sensor 44 in FIG. 3). The compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2C:
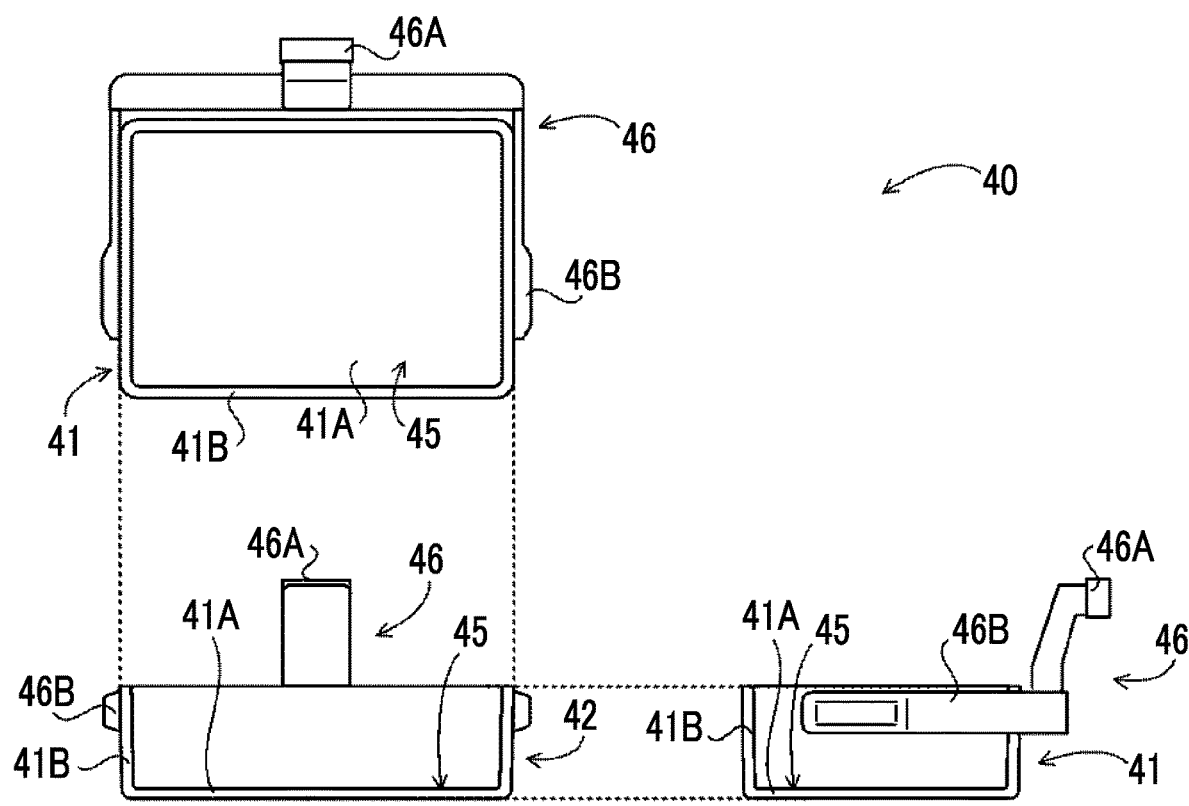
FIG. 2C is a three-view diagram illustrating an example of a compression plate according to the embodiment.

As a specific example, the compression plate 40 that can be attached to the mammography apparatus 10 according to this embodiment will be described with reference to FIG. 2C. FIG. 2C is a three-view diagram illustrating an example of the compression plate 40 according to this embodiment. The three-view diagram illustrated in FIG. 2C includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2C, the compression plate 40 according to this embodiment includes a compression portion 41 and the support portion 46.

The compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height. The compression portion 41 has a projection surface 45 onto which a projection image P is projected by a projector 48 which will be described below. For example, in this embodiment, a surface (upper surface) of the bottom portion 41A of the compression portion 41 which faces the radiation emitting unit 37 is the projection surface 45. In addition, for example, the position of the projection surface 45 of the compression plate 40 is not limited to this aspect. For example, the projection surface 45 may be a surface of the bottom portion 41A of the compression portion 41 which comes into contact with the breast or a surface of the wall portion 41B.

It is preferable that the compression plate 40 is optically transparent in order to check positioning or a compressed state. In addition, the compression plate 40 is made of a material having high transmittance for the radiation R. Further, in a case in which light is incident on the projection surface 45, most of the light (for example, 90%) is transmitted and a portion (for example, 10%) of the light is specularly reflected from the surface of an object such that an incident angle and a reflection angle are equal to each other, in order to display an image corresponding to the projection image P projected from the projector 48. For example, a surface of the bottom portion 41A of the compression plate 40 which faces the radiation source 37R may be roughened to form the projection surface 45. In addition, for example, a specular reflection sheet may be attached to the surface of the compression plate 40 to form the projection surface 45. Further, in a case in which the projection surface 45 is a smooth surface such as a case in which a specular reflection sheet is attached, a surface of the compression plate 40 that comes into contact with the subject, such as the breast, may be the projection surface 45.

On the other hand, the support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

Further, the projector 48 that projects the projection image P onto the projection surface 45 of the compression plate 40 is provided at a position of the arm portion 32 which is away from the subject below the radiation emitting unit 37. The projector 48 according to this embodiment is an example of an image projection unit according to the present disclosure. Known projectors, such as a liquid crystal projector, a Digital Light Processing (DLP) (registered trademark) projector, and a laser projector, can be used as the projector 48. As illustrated in FIG. 3, the projector 48 according to this embodiment includes a power supply unit 48A and a projection unit 48B. In the projector 48, the turn-on and turn-off of the power supply unit 48A are controlled in response to an instruction from the control unit 20 which will be described below. Further, the projection image P is projected from the projection unit 48B onto the projection surface 45 of the compression plate 40 in response to an instruction from a control unit 20.

Furthermore, the control unit 20, a storage unit 22, an interface (IF) unit 24, an operation unit 26, and a display unit 27 illustrated in FIG. 3 are provided in the imaging table 30 of the mammography apparatus 10 according to this embodiment. The control unit 20, the storage unit 22, the I/F unit 24, the operation unit 26, the display unit 27, the radiation detector 28, the compression plate driving unit 42, the compression plate detection sensor 44, and the projector 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by the radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a projection control program 51 (which will be described below) executed by the CPU 50A are stored in the ROM 50B in advance. The RAM 50C temporarily stores various kinds of data. The CPU 50A according to this embodiment is an example of a processor according to the present disclosure. The projection control program 51 according to this embodiment is an example of a control program according to the present disclosure.

For example, the image data of the radiographic image captured by the mammography apparatus 10 and various other kinds of information are stored in the storage unit 52. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
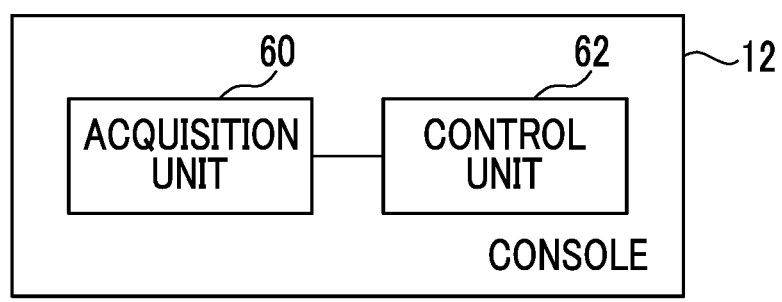
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises an acquisition unit 60 and a control unit 62. For example, in the console 12 according to this embodiment, the CPU 50A of the control unit 50 executes the projection control program 51 stored in the ROM 50B to function as the acquisition unit 60 and the control unit 62.

The acquisition unit 60 has a function of acquiring inclination information indicating the inclination of the imaging surface 30A of the imaging table 30. The inclination information acquired by the acquisition unit 60 is output to the control unit 62. As described above, in the mammography apparatus 10 according to this embodiment, the imaging table 30 is supported by the arm portion 32, and the imaging surface 30A of the imaging table 30 is inclined by the rotation of the arm portion 32. Therefore, in a case in which the arm portion 32 is inclined, the imaging surface 30A of the imaging table 30 is also inclined.

In the case of the CC imaging, the arm portion 32 is not inclined with respect to the subject. In the case of the MLO imaging, the arm portion 32 is inclined with respect to the subject. The acquisition unit 60 acquires the inclination information indicating whether the arm portion 32 is not inclined, is inclined in the negative direction (see FIG. 2B), or is inclined in the positive direction. In addition, for example, the acquisition unit 60 according to this embodiment acquires, as the inclination information, information indicating whether the CC imaging or the MLO imaging is performed and whether the left breast or the right breast is imaged with reference to the imaging menu. Specifically, in a case in which the inclination information indicates that the CC imaging is performed, it indicates that the imaging surface 30A of the imaging table 30 is not inclined, in other words, the arm portion 32 is not inclined.

Further, in a case in which the inclination information indicates that the MLO imaging is performed and the right breast is imaged, it indicates that the imaging surface 30A of the imaging table 30 is inclined to the left, in other words, the arm portion 32 is inclined in the negative direction. Furthermore, in a case in which the inclination information indicates that the MLO imaging is performed and the left breast is imaged, it indicates that the imaging surface 30A of the imaging table 30 is inclined to the right, in other words, the arm portion 32 is inclined in the positive direction. In addition, a method for acquiring the inclination information in the acquisition unit 60 is not limited to this embodiment. For example, the acquisition unit 60 may acquire, as the inclination information, the angle at which the imaging surface 30A of the imaging table 30 is inclined. Further, for example, the acquisition unit 60 may acquire, as the inclination information, information indicating the rotation angle of the arm portion 32.

The control unit 62 has a function of performing control to adjust information displayed on the projection surface 45 by the projection of the projection image P onto the projection surface 45 of the compression plate 40 by the radiation emitting unit 37 according to the inclination indicated by the inclination information. Specifically, the control unit 62 performs control to switch the direction of the information displayed by the projection of the projection image P according to the inclination.

The user compresses the positioned breast of the subject with the compression plate 40. Specifically, in a case in which the compression plate 40, which has been moved in the compression direction from a state in which the breast positioned on the imaging surface 30A of the imaging table 30 is compressed by the user's hand, approaches the breast, the hand is pulled out from between the compression plate 40 and the breast, and the breast is compressed by the compression plate 40.

In the case of the CC imaging, as illustrated in FIG. 2B, the imaging surface 30A of the imaging table 30 faces directly upward. Therefore, the user stands on either the left or right side of the subject and performs positioning. On the other hand, in the case of the MLO imaging of the right breast, as illustrated in FIG. 2B, the imaging surface 30A of the imaging table 30 is inclined to the left. Therefore, the user stands on the left side of the subject and performs positioning. Further, in the case of the MLO imaging of the left breast, as illustrated in FIG. 2B, the imaging surface 30A of the imaging table 30 is inclined to the right. Therefore, the user stands on the right side of the subject and performs positioning. In other words, in a case in which the MLO imaging is performed, the user stands on the side where the radiation source 37R is located and performs positioning.

That is, the standing position of the user who performs positioning varies depending on the inclination of the imaging surface 30A of the imaging table 30. Therefore, the control unit 62 according to this embodiment performs control to adjust the direction of the information displayed by the projection image P according to the inclination of the imaging surface 30A of the imaging table 30 to display the projection image P such that it is easy for the user to see the projection image P.

In addition, in a case in which the information displayed by the projection image P is character information, specifically, in a case in which characters and numbers are displayed, the direction of the information displayed as described above is adjusted such that it is easy for the user who performs positioning to see the information. On the other hand, the direction of the breast positioned on the imaging table 30 does not change regardless of the inclination of the imaging surface 30A of the imaging table 30. Therefore, in a case in which the information displayed by the projection image P is information indicating at least one of the shape or position of the breast, such as a skin line, the control unit 62 according to this embodiment performs control such that the information is displayed in the same direction regardless of the inclination of the imaging surface 30A of the imaging table 30.

Figure 5A:
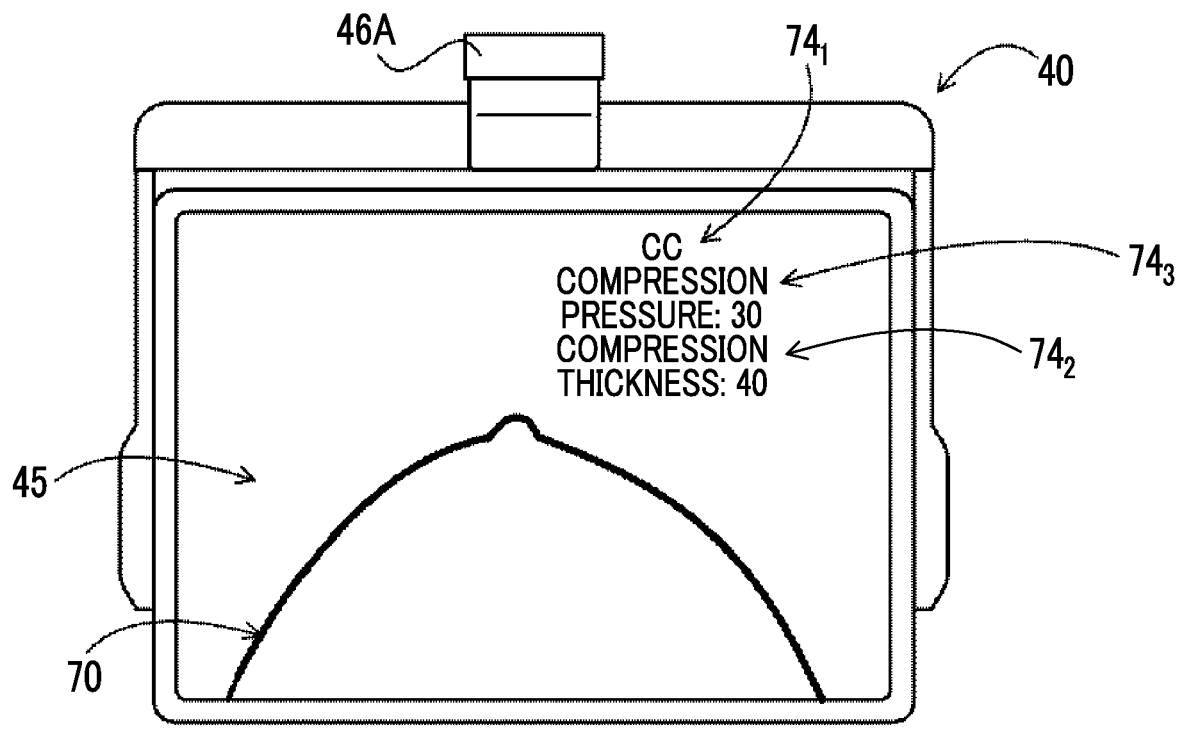
FIG. 5A is a diagram illustrating an example of a display state of information displayed on a projection surface by a projection image in the CC imaging.
Figure 5B:
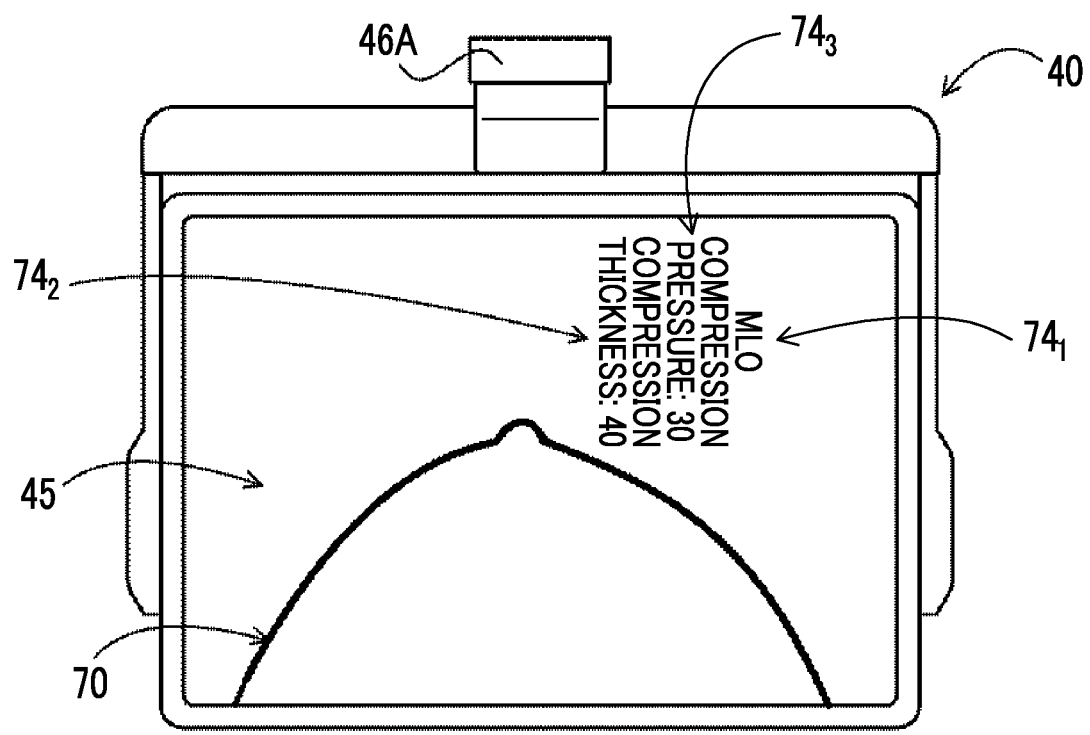
FIG. 5B is a diagram illustrating an example of a display state of information displayed on the projection surface by a projection image in the MLO imaging of a right breast.
Figure 5C:
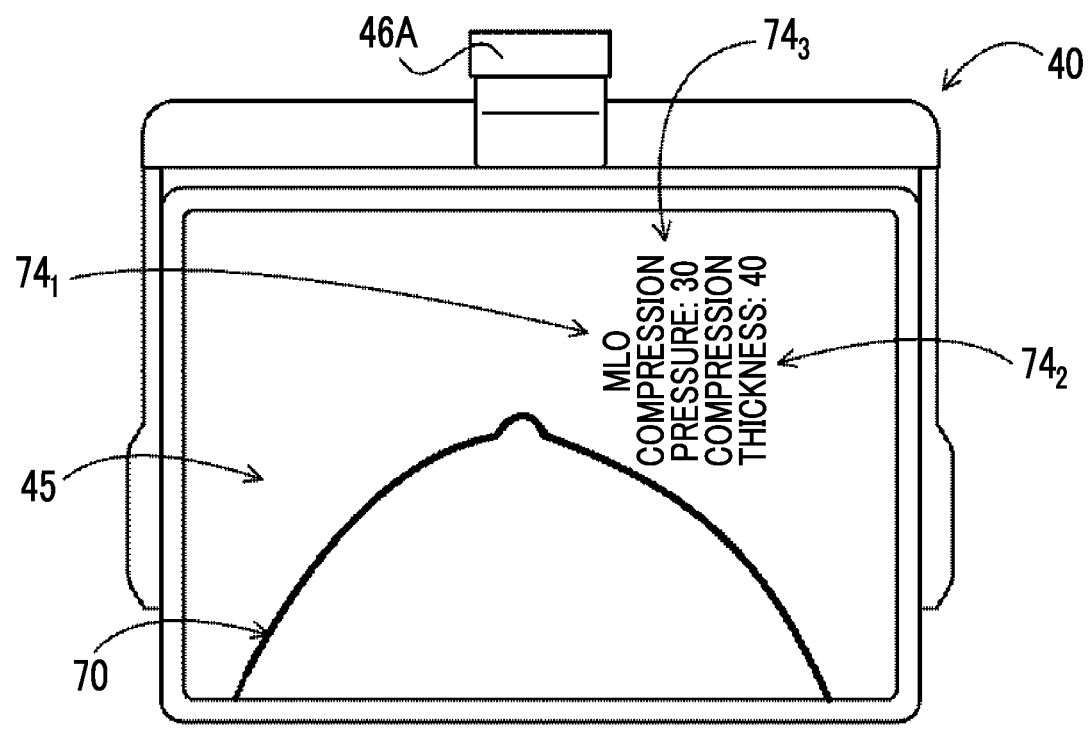
FIG. 5C is a diagram illustrating an example of a display state of information displayed on the projection surface by a projection image in the MLO imaging of a left breast.

FIGS. 5A to 5C illustrate an example of the display state of information displayed on the projection surface 45 by the projection image P under the control of the control unit 62. Each of FIGS. 5A to 5C illustrates a state in which a skin line 70 indicating the shape of the breast is displayed. In addition, each of FIGS. 5A to 5C illustrates a state in which three types of character information, that is, character information $74_1$ indicating the type of imaging corresponding to the degree of inclination of the imaging surface 30A of the imaging table 30, character information $74_2$ indicating the thickness of the breast compressed by the compression plate 40, and character information $74_3$ indicating the compression pressure against the breast compressed by the compression plate 40 are displayed. Further, the "thickness of the breast" is the thickness of the breast compressed by the compression plate 40, corresponds to a distance between the compression plate 40 and the imaging table 30, and also corresponds to the height from the imaging surface 30A of the imaging table 30 to the compression plate 40. Furthermore, the "compression pressure" is compression pressure related to the compression plate 40.

FIG. 5A illustrates an example of the display state of the information displayed on the projection surface 45 by the projection image P in the CC imaging. In addition, the CC imaging is controlled in the state illustrated in FIG. 5A regardless of whether the left breast or the right breast is imaged. As illustrated in FIG. 5A, in the case of the CC imaging, each of the character information items $74_1$ to $74_3$ is displayed while facing the chest wall side, in other words, the front side of the mammography apparatus 10.

FIG. 5B illustrates an example of the display state of the information displayed on the projection surface 45 by the projection image Pin the MLO imaging of the right breast. As illustrated in FIG. 5B, in the case of the MLO imaging of the right breast, each of the character information items $74_1$ to $74_3$ is displayed while facing the left side of the subject (mammography apparatus 10).

FIG. 5C illustrates an example of the display state of the information displayed on the projection surface 45 by the projection image P in the MLO imaging of the left breast. As illustrated in FIG. 5C, in the case of the MLO imaging of the left breast, each of the character information items $74_1$ to $74_3$ is displayed while facing the right side of the subject (mammography apparatus 10).

On the other hand, as illustrated in FIGS. 5A to 5C, the skin lines 70 are displayed in the same direction. Specifically, the shapes of the breast indicated by the skin lines 70 are shapes corresponding to the CC imaging, the MLO imaging, and the left and right sides of the breast. However, the shapes are displayed in the same direction regardless of the inclination of the imaging surface 30A of the imaging table 30.

Figure 6:
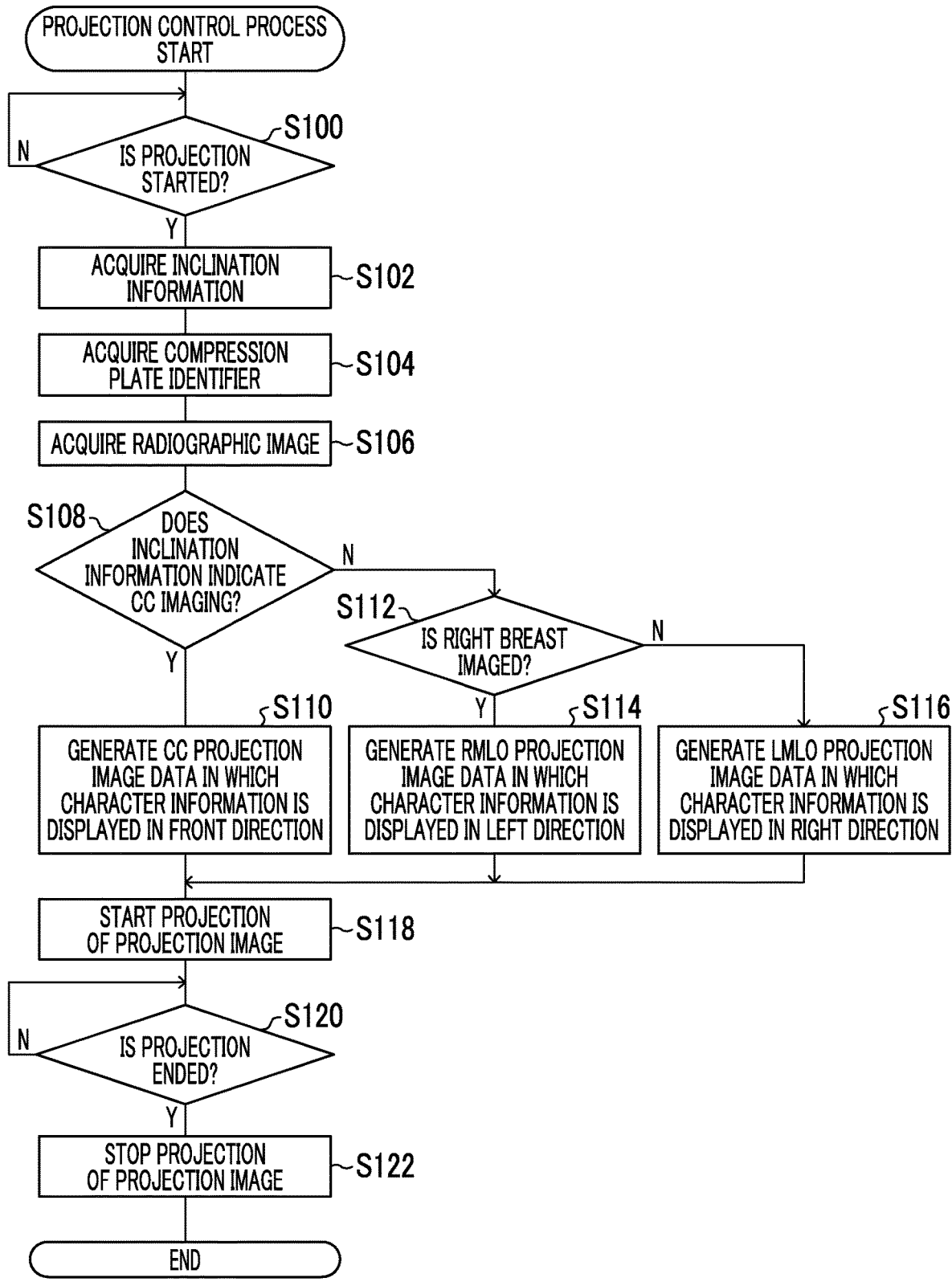
FIG. 6 is a flowchart illustrating an example of the flow of a projection control process according to a first embodiment.

Next, the operation of the console 12 in the projection of the projection image P by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selected imaging menu, a projection control process illustrated in FIG. 6 is performed. In the console 12 according to this embodiment, for example, the CPU 50A of the control unit 50 executes the projection control program 51 stored in the ROM 50B to perform the projection control process whose example is illustrated in FIG. 6. FIG. 6 is a flowchart illustrating an example of the flow of the projection control process performed in the console 12 according to this embodiment.

In Step S100 of FIG. 6, the control unit 62 determines whether or not to start the projection of the projection image P. For example, in this embodiment, in a case in which the user wants to start the projection of the projection image P onto the projection surface 45, the user inputs a projection start instruction through the operation unit 26 of the mammography apparatus 10. The mammography apparatus 10 outputs a projection start instruction signal through the I/F unit 24. In a case in which the projection start instruction signal is input to the console 12, the control unit 62 starts the projection of the projection image P. Therefore, the determination result in Step S100 is "No" until the projection start instruction signal is input to the console 12. On the other hand, in a case in which the projection start instruction signal is input to the console 12, the determination result in Step S100 is "Yes", and the process proceeds to Step S102.

In Step S102, the acquisition unit 60 acquires the inclination information indicating the inclination of the imaging surface 30A of the imaging table 30 as described above. The acquisition unit 60 according to this embodiment acquires, as the inclination information, information indicating whether the CC imaging or the MLO imaging is performed and whether the left breast or the right breast is imaged with reference to the imaging menu.

Then, in Step S104, the control unit 62 acquires a compression plate identifier. As described above, in the mammography apparatus 10, the compression plate detection sensor 44 reads the compression plate identifier of the compression plate 40 having the support portion 46 attached to the compression unit 36. Then, the control unit 62 according to this embodiment acquires the compression plate identifier read by the compression plate detection sensor 44 from the mammography apparatus 10.

Then, in Step S106, the control unit 62 acquires a radiographic image used to generate the projection image P. For example, in this embodiment, the control unit 62 generates the projection image P from the radiographic image of the breast. Therefore, the control unit 62 acquires the radiographic image of the breast.

It is preferable that the radiographic image acquired by the control unit 62 is the radiographic image of the breast of the subject captured in the past. For example, the radiographic image acquired by the control unit 62 may be a radiographic image of the same subject as that in the current imaging which was captured in the past and in which at least one of the left or right breast, inclination information (the CC imaging or the MLO imaging), or the type of the compression plate 40 indicated by the compression plate identifier is the same as that in the current imaging. Further, for example, the radiographic image acquired by the control unit 62 may be a radiographic image of the same subject as that in the current imaging which was captured in the past and in which at least one of the opposite breast imaged immediately before the current imaging, inclination information (the CC imaging or the MLO imaging), or the type of the compression plate 40 indicated by the compression plate identifier is the same as that in the current imaging. In a case in which the radiographic image of the opposite breast is used in this way, an image obtained by reversing the radiographic image or the image indicating the skin line extracted from the radiographic image may be applied as the projection image P in the imaging of the opposite breast.

In addition, in some cases, the radiographic image of the breast of the same subject as that in the current imaging is absent, for example, in the storage unit 52 of the console 12 or a picture archiving and communication system (PACS). In this case, for example, the control unit 62 may acquire a radiographic image captured in a state in which a standard breast corresponding to the type of the compression plate 40 or the like is compressed into an ideal state by the compression plate 40. Specifically, the radiographic image captured in a state in which the standard breast is compressed into the ideal state by the compression plate 40 may be stored in, for example, the storage unit 52 so as to be associated with the compression plate identifier indicating the compression plate 40 used for imaging, and the control unit 62 may acquire the radiographic image corresponding to the compression plate identifier acquired in Step S104 from, for example, the storage unit 52.

Then, in Step S108, the control unit 62 determines whether or not the inclination information acquired in Step S102 indicates the CC imaging. In a case in which the inclination information indicates the CC imaging, the determination result in Step S108 is "Yes", and the process proceeds to Step S110.

In Step S110, the control unit 62 generates CC projection image data which includes the skin line and in which the character information is displayed in the front direction and then proceeds to Step S118. In addition, a method for generating the CC projection image data in the control unit 62 is not particularly limited. For example, the control unit 62 according to this embodiment generates a skin line image which indicates the skin line indicating the shape of the breast from the radiographic image acquired in Step S106. In addition, a method for generating the skin line image in the control unit 62 is not particularly limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line. In addition, for example, JP2010-051456A discloses a method which divides a radiographic image of the breast into a breast region and a blank region on the basis of the density of each pixel of the radiographic image and connects the pixels which are the boundary points between the breast region and the blank region to generate a skin line.

In addition, in a case in which the skin line image generated from the radiographic image acquired by the control unit 62 is projected as the projection image P without any change, the size of the skin line image may be different from the size of the projection surface 45. In a case in which the radiographic image captured in the past is larger than the projection surface 45, the control unit 62 may generate a skin line image based on the shape of the breast indicated by a partial region of the radiographic image which corresponds to the size of the projection surface 45. In other words, the control unit 62 may cut a partial region corresponding to the size of the projection surface 45 in the radiographic image captured in the past and generate a skin line image on the basis of the cut image. In addition, in many cases, the mammography apparatus 10 captures an image including the chest wall side. Therefore, the region to be cut is preferably a partial region on the chest wall side. Further, it is preferable that the region to be cut is a partial region including the center of the shape of the breast included in the radiographic image in the left-right direction.

Furthermore, in a case in which the radiographic image captured in the past is smaller than the projection surface 45, the control unit 62 may generate a skin line image in which the shape of the breast outside the radiographic image has been complemented on the basis of the shape of the breast indicated by the radiographic image. A known image complementing method can be applied as the complementing method. For example, the control unit 62 may complement an extension line on the basis of the curvature of the skin line of a portion generated on the basis of the radiographic image captured in the past. Further, for example, the control unit 62 may complement a tangent line of the skin line of the portion generated on the basis of the radiographic image as the extension line.

Further, in a case in which the size of the radiographic image captured in the past and the size of the projection surface 45 are not matched with each other, the control unit 62 may generate a skin line image based on the shape of the breast indicated by an image obtained by enlarging or reducing the radiographic image captured in the past according to the size of the projection surface 45. For example, an enlargement and reduction ratio may be predetermined for each combination of the size of the radiographic image and the size of the projection surface 45.

Further, the control unit 62 combines the image indicating the character information items $74_1$, $74_2$, and $74_3$ and the skin line image in a state in which the characters are displayed in the front direction to generate CC projection image data indicating the projection image P. In addition, in this embodiment, each of information indicating the type of imaging represented by the character information $74_1$, information indicating the thickness of the breast represented by the character information $74_2$, and information indicating the compression pressure represented by the character information $74_3$ is associated with the radiographic image in advance.

On the other hand, in Step S108, in a case in which the inclination information acquired in Step S102 does not indicate the CC imaging, in other words, in a case in which the inclination information indicates the MLO imaging, the determination result is "No", and the process proceeds to Step S112.

Then, in Step S112, the control unit 62 determines whether or not the inclination information acquired in the Step S102 indicates the imaging of the right breast. In a case in which the inclination information indicates the imaging of the right breast, the determination result in Step S112 is "Yes", and the process proceeds to Step S114.

The control unit 62 generates RMLO projection image data which includes the skin line and in which the character information is displayed in the left direction in Step S114 and then proceeds to Step S118. In addition, a method for generating the RMLO projection image data in the control unit 62 is not particularly limited. For example, first, the control unit 62 according to this embodiment generates a skin line image which indicates a skin line indicating the shape of the breast from the radiographic image acquired in Step S106, as in Step S110. Further, the control unit 62 combines the image indicating the character information items $74_1$, $74_2$, and $74_3$ and the skin line image in a state in which the characters are displayed in the left direction to generate RMLO projection image data indicating the projection image P.

On the other hand, in a case in which the inclination information acquired in Step S102 does not indicate the imaging of the right breast in Step S112, in other words, in a case in which the inclination information indicates the imaging of the left breast, the determination result is "No", and the process proceeds to Step S116.

The control unit 62 generates LMLO projection image data which includes the skin line and in which the character information is displayed in the right direction in Step S116 and then proceeds to Step S118. In addition, a method for generating the LMLO projection image data in the control unit 62 is not particularly limited. For example, first, the control unit 62 according to this embodiment generates a skin line image which indicates a skin line indicating the shape of the breast from the radiographic image acquired in Step S106, as in Steps S110 and S114. Further, the control unit 62 combines the image indicating the character information items $74_1$, $74_2$, and $74_3$ and the skin line image in a state in which the characters are displayed in the right direction to generate LMLO projection image data indicating the projection image P.

Furthermore, in the following description, in a case in which the CC projection image data, the RMLO projection image data, and the LMLO projection image data are collectively referred to, they are simply referred to as "projection image data".

Then, in Step S118, the control unit 62 starts the projection of the projection image P. Specifically, the control unit 62 outputs the projection image data indicating the projection image P to the mammography apparatus 10 through the I/F unit 54. In the mammography apparatus 10, in a case in which the projection image data is input, the control unit 20 performs control to direct the projection unit 48B of the projector 48 to project the projection image P corresponding to the projection image data. Information corresponding to the projection image P is displayed on the projection surface 45 of the compression plate 40 attached to the compression unit 36 of the mammography apparatus 10 by this control.

Specifically, in a case in which the CC projection image data is generated in Step S110, the control unit 62 outputs the CC projection image data to the mammography apparatus 10 in Step S118. In the mammography apparatus 10, the projector 48 projects the projection image P corresponding to the CC projection image data. The state illustrated in FIG. 5A is displayed on the projection surface 45 of the compression plate 40 by the projection of the projection image P.

In addition, in a case in which the RMLO projection image data is generated in Step S114, the control unit 62 outputs the RMLO projection image data to the mammography apparatus 10 in Step S118. In the mammography apparatus 10, the projector 48 projects the projection image P corresponding to the RMLO projection image data. The state illustrated in FIG. 5B is displayed on the projection surface 45 of the compression plate 40 by the projection of the projection image P.

In a case in which the LMLO projection image data is generated in Step S116, the control unit 62 outputs the LMLO projection image data to the mammography apparatus 10 in Step S118. In the mammography apparatus 10, the projector 48 projects the projection image P corresponding to the LMLO projection image data. The state illustrated in FIG. 5C is displayed on the projection surface 45 of the compression plate 40 by the projection of the projection image P.

Then, in Step S120, the control unit 62 determines whether or not to end the projection of the projection image P. For example, in this embodiment, in a case in which end conditions are satisfied, the projection of the projection image P ends. The end conditions include, for example, a condition in which the projection of the projection image P ends in a case in which the user inputs an instruction to end the projection of the projection image P. Further, for example, in a case in which the compression of the breast by the compression plate 40 is completed, the user inputs an instruction to emit the radiation R. Therefore, the end conditions include conditions such as the timing when the emission of the radiation R by the radiation source 37R starts and the timing when the emission of the radiation R by the radiation source 37R ends. The determination result in Step S120 is "No" until the end conditions are satisfied. On the other hand, in a case in which the end conditions are satisfied, the determination result in Step S120 is "Yes", and the process proceeds to Step S122.

In Step S122, the control unit 62 ends the projection of the projection image P. Specifically, the control unit 62 outputs a projection end signal for ending the projection of the projection image P to the mammography apparatus 10 through the I/F unit 54. In the mammography apparatus 10, in a case in which the projection end signal is input, the control unit 20 ends the projection of the projection image P by the projection unit 48B of the projector 48. Specifically, the emission of projection light for projecting the projection image P is stopped. In a case in which the projection of the projection image P is ended, the supply of power to the power supply unit 48A is cut off to turn off the power supply unit 48A. In a case in which the process in Step S122 ends, the image processing illustrated in FIG. 6 ends.

As described above, the console 12 according to this embodiment performs control such that the direction of the character information displayed on the projection surface 45 of the compression plate 40 by the projection image P projected by the projector 48 is different between a case in which the CC imaging is performed and a case in which the MLO imaging is performed. In addition, in the MLO imaging, the console 12 performs control such that the direction of the character information displayed on the projection surface 45 of the compression plate 40 by the projection image P is different between a case in which the right breast is imaged and a case in which the left breast is imaged.

The inclinations of the imaging surface 30A of the imaging table 30 are different in the CC imaging, the MLO imaging of the right breast, and the MLO imaging of the left breast. In this embodiment, control is performed such that the direction of the character information displayed on the projection surface 45 of the compression plate 40 by the projection image P differs depending on the inclination of the imaging surface 30A of the imaging table 30 in each imaging operation. With this configuration, in the console 12 according to this embodiment, the character information is displayed in a direction in which it is easy for the user to position the breast according to the imaging surface 30A of the imaging table 30. Therefore, according to the console 12 of this embodiment, it is possible to reduce the burden on the user who positions the breast.

Second Embodiment

In this embodiment, a difference in the control of the display state of the projection image P from the first embodiment will be described.

In some cases, the irradiation field varies depending on the inclination of the imaging surface 30A of the imaging table 30 or the type of the compression plate 40.

Figure 7A:
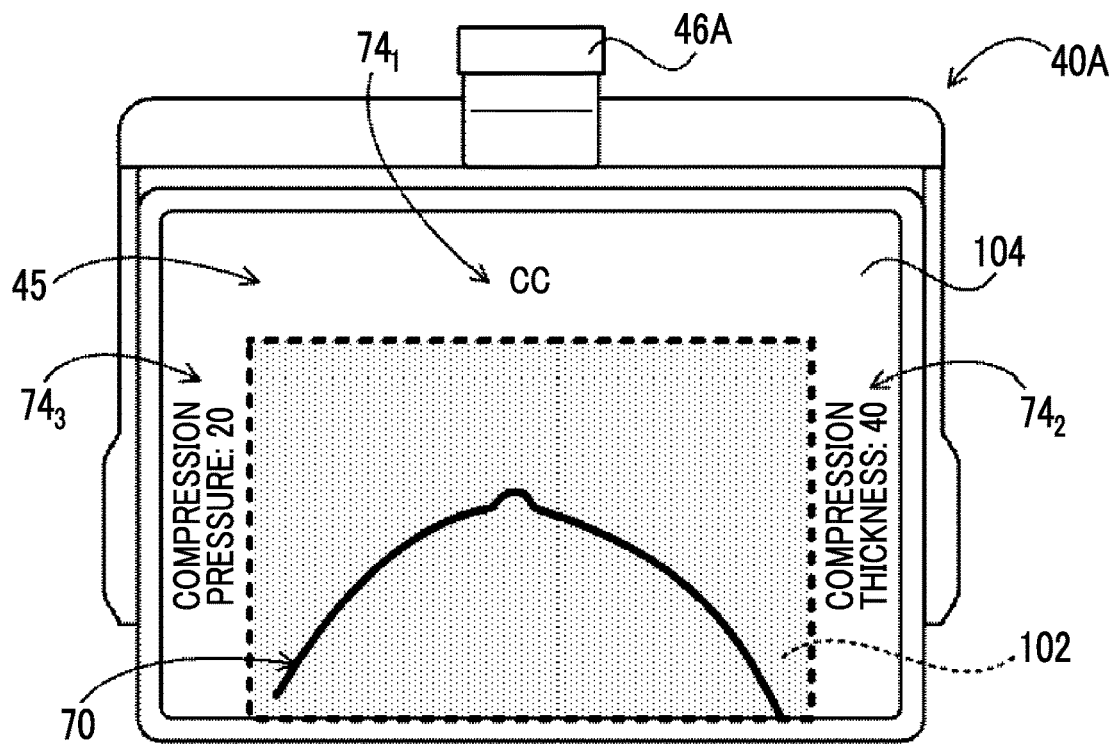
FIG. 7A is a diagram illustrating an example of a display state of information displayed on the projection surface by a projection image in a case in which an irradiation field is smaller than the projection surface in the CC imaging.
Figure 7B:
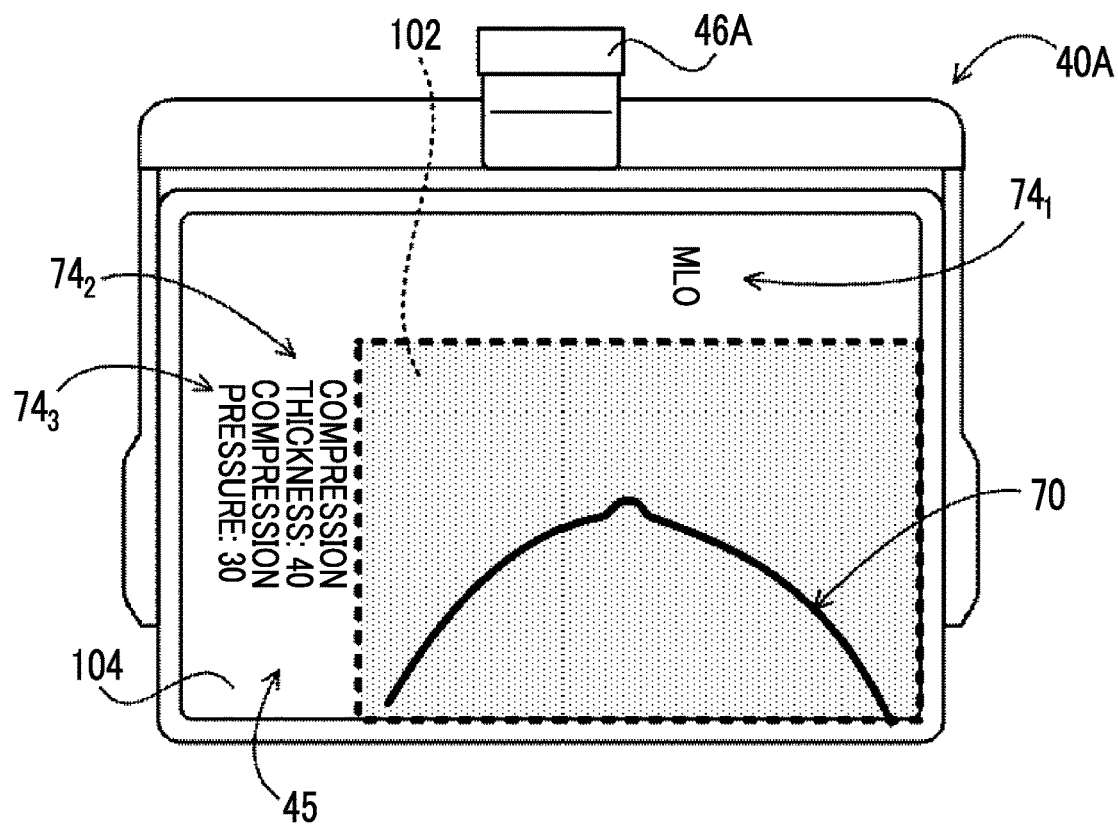
FIG. 7B is a diagram illustrating an example of a display state of information displayed on the projection surface by a projection image in a case in which the irradiation field is smaller than the projection surface in the MLO imaging of the right breast.
Figure 7C:
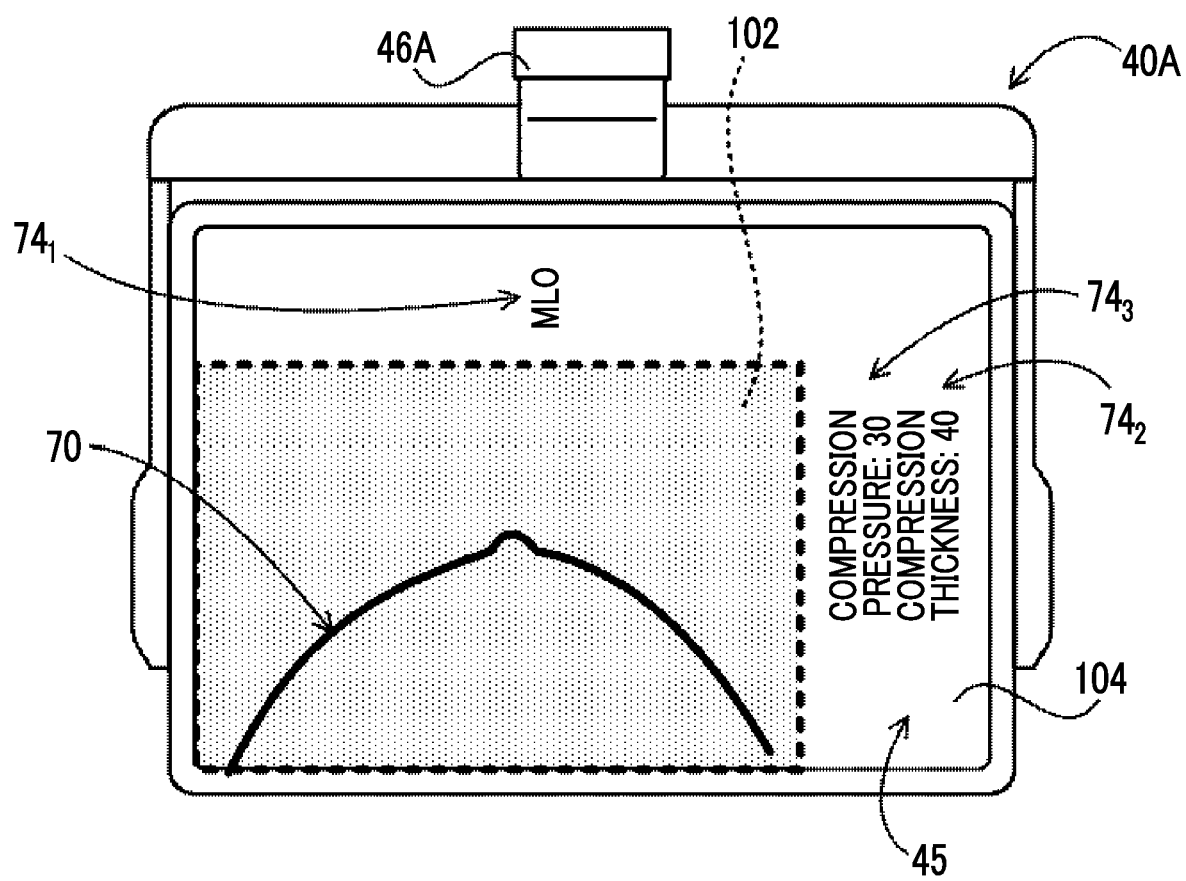
FIG. 7C is a diagram illustrating an example of a display state of information displayed on the projection surface by a projection image in a case in which the irradiation field is smaller than the projection surface in the MLO imaging of the left breast.

For example, FIGS. 7A to 7C illustrate an example of the display state of information displayed on the projection surface 45 of a compression plate 40A used for imaging a relatively small breast. In FIGS. 7A to 7C, a region of the irradiation field with respect to the projection surface 45 of the compression plate 40A used to compress the relatively small breast is illustrated as an irradiation field 102. FIG. 7A illustrates the case of the CC imaging, and the position of the irradiation field 102 is on the chest wall side and is at the center. FIG. 7B illustrates the case of the MLO imaging of the right breast, and the position of the irradiation field 102 is on the chest wall side and leans to the right. Further, FIG. 7C illustrates the case of the MLO imaging of the left breast, and the position of the irradiation field 102 is on the chest wall side and leans to the left. As described above, in the compression plate 40A used to image the relatively small breast, the positions of the region of the irradiation field with respect to the projection surface 45 of the compression plate 40 are different in the CC imaging, the MLO imaging of the right breast, and the MLO imaging of the left breast.

Furthermore, as illustrated in FIGS. 7A to 7C, in the imaging of the relatively small breast, the size of the irradiation field 102 is smaller than the size of the projection surface 45 of the compression plate 40A, a partial region of the projection surface 45 is the irradiation field 102, and the skin line 70 is displayed in the irradiation field 102. In addition, the character information is displayed in a direction corresponding to the inclination of the imaging surface 30A of the imaging table 30 in a region 104 of the projection surface 45 outside the irradiation field.

Specifically, in the case of the CC imaging, as illustrated in FIG. 7A, the skin line is displayed in the irradiation field 102 at the center of the projection surface 45. In addition, the character information $74_1$ is displayed in the front direction in the region 104 which is outside the irradiation field and is opposite to the chest wall, the character information $74_2$ is displayed in the front direction on the right side of the irradiation field 102, and the character information $74_3$ is displayed in the front direction on the left side of the irradiation field 102.

Further, in the case of the MLO imaging of the right breast, as illustrated in FIG. 7B, the skin line is displayed in the irradiation field 102 on the right side of the projection surface 45. Furthermore, the character information $74_1$ is displayed in the left direction in the region 104 which is outside the irradiation field and is opposite to the chest wall, and the character information $74_2$ and the character information $74_3$ are displayed in the left direction on the left side of the irradiation field 102.

Moreover, in the case of the MLO imaging of the left breast, as illustrated in FIG. 7C, the skin line is displayed in the irradiation field 102 on the left side of the projection surface 45. In addition, the character information $74_1$ is displayed in the right direction in the region 104 which is outside the irradiation field and is opposite to the chest wall, and the character information $74_2$ and the character information $74_3$ are displayed in the right direction on the right side of the irradiation field 102.

Figure 8A:
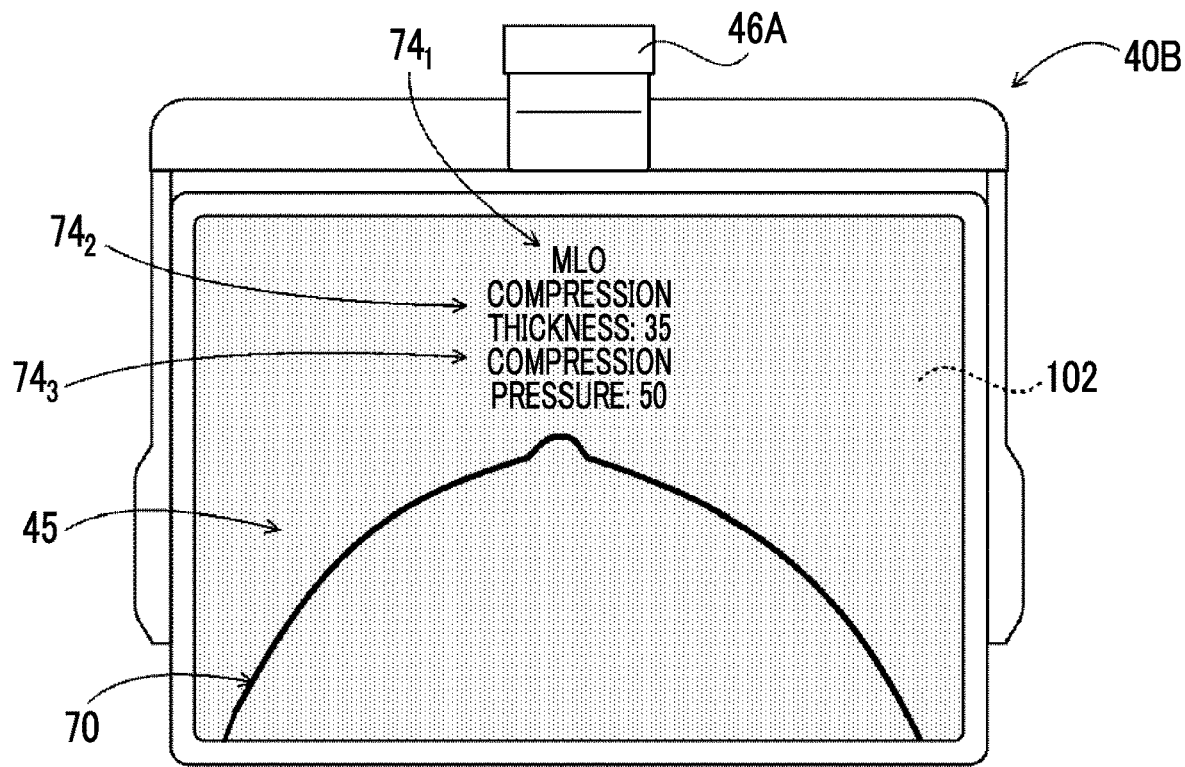
FIG. 8A is a diagram illustrating an example of a display state of information displayed on the projection surface by a projection image in a case in which the size of the irradiation field is equal to or larger than the size of the projection surface in the CC imaging.
Figure 8B:
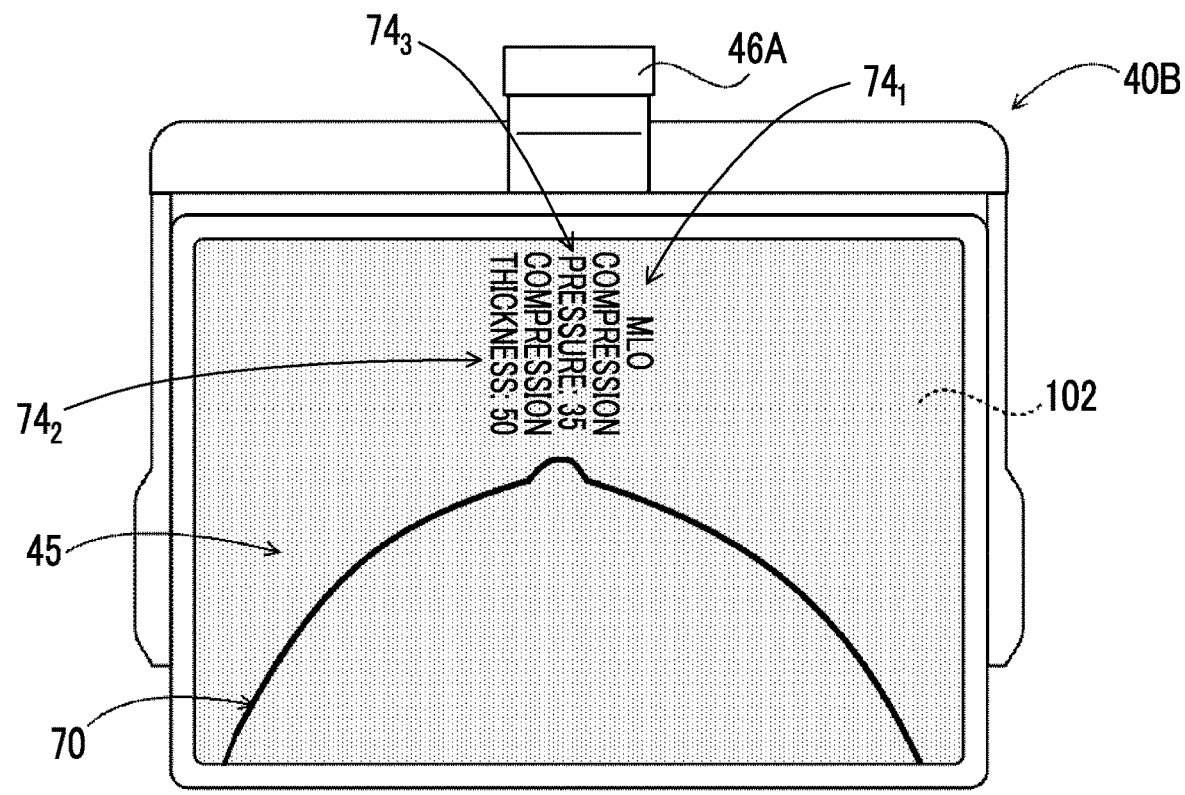
FIG. 8B is a diagram illustrating an example of a display state of information displayed on the projection surface by a projection image in a case in which the size of the irradiation field is equal to or larger than the projection surface in the MLO imaging of the right breast.
Figure 8C:
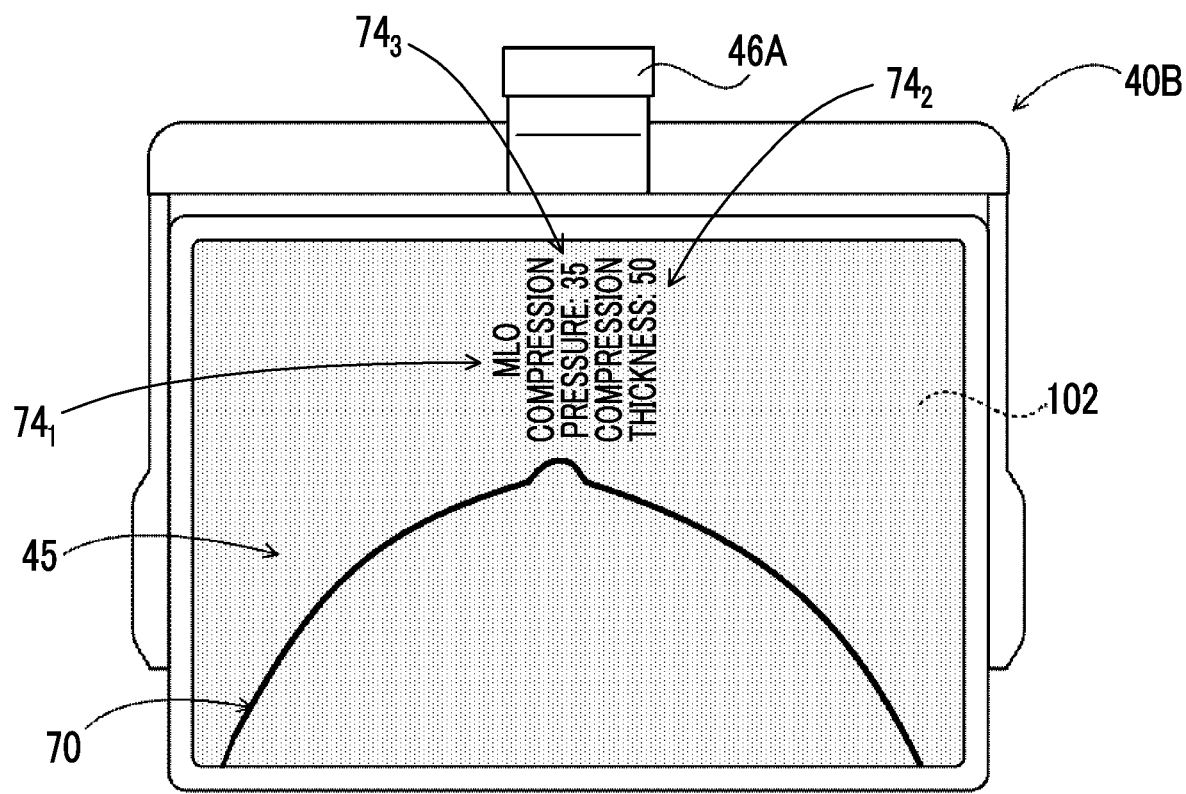
FIG. 8C is a diagram illustrating an example of a display state of information displayed on the projection surface by a projection image in a case in which the size of the irradiation field is equal to or larger than the projection surface in the MLO imaging of the left breast.

Further, as another example, FIGS. 8A to 8C illustrate an example of the display state of information displayed on the projection surface 45 of a compression plate 40B used to image a relatively large breast. FIG. 8A illustrates the case of the CC imaging, FIG. 8B illustrates the case of the MLO imaging of the right breast, and FIG. 8C illustrates the case of the MLO imaging of the left breast. As illustrated in FIGS. 8A to 8C, in the compression plate 40B used to image the relatively large breast, the position of the irradiation field 102 is the same regardless of the CC imaging, the MLO imaging of the right breast, and the MLO imaging of the left breast, and the size of the irradiation field 102 is equal to or larger than the size of the projection surface 45. In addition, the case in which the size of the irradiation field 102 and the size of the projection surface 45 are equal to each other may be a case in which design errors or the like are ignored and the sizes are regarded as being equal to each other. For example, in a case in which a difference between the size of the irradiation field 102 and the size of the projection surface 45 is within ±10% of the area of the projection surface 45, the sizes are regarded as being equal to each other.

Since the size of the irradiation field 102 is equal to or larger than the size of the projection surface 45 of the compression plate 40, the positions where the character information items $74_1$ to $74_3$ are displayed are the same regardless of the CC imaging, the MLO imaging of the right breast, and the MLO imaging of the left breast as illustrated in FIGS. 8A to 8C. Specifically, the character information items $74_1$ to $74_3$ are displayed in a region of the irradiation field 102 which is opposite to the chest wall.

On the other hand, as illustrated in FIGS. 8A to 8C, the direction in which the character information items $74_1$ to $74_3$ are displayed corresponds to the inclination of the imaging surface 30A of the imaging table 30 in each of the CC imaging, the MLO imaging of the right breast, and the MLO imaging of the left breast as described above. Specifically, in the case of the CC imaging, the character information items $74_1$ to $74_3$ are displayed in the front direction as illustrated in FIG. 8A. Further, in the case of the MLO imaging of the right breast, the character information items $74_1$ to $74_3$ are displayed in the right direction as illustrated in FIG. 8B. Further, in the case of the MLO imaging of the left breast, the character information items $74_1$ to $74_3$ are displayed in the left direction as illustrated in FIG. 8C.

Therefore, the control unit 62 according to this embodiment has a function of controlling the display positions of the character information items $74_1$ to $74_3$ as illustrated in FIGS. 7A to 7C and FIGS. 8A to 8C according to the size of the irradiation field 102 with respect to the projection surface 45. In addition, since the other configurations of the mammography apparatus 10 and the console 12 according to this embodiment are the same as those of the mammography apparatus 10 and the console 12 according to the first embodiment, the description thereof will not be repeated.

Figure 9A:
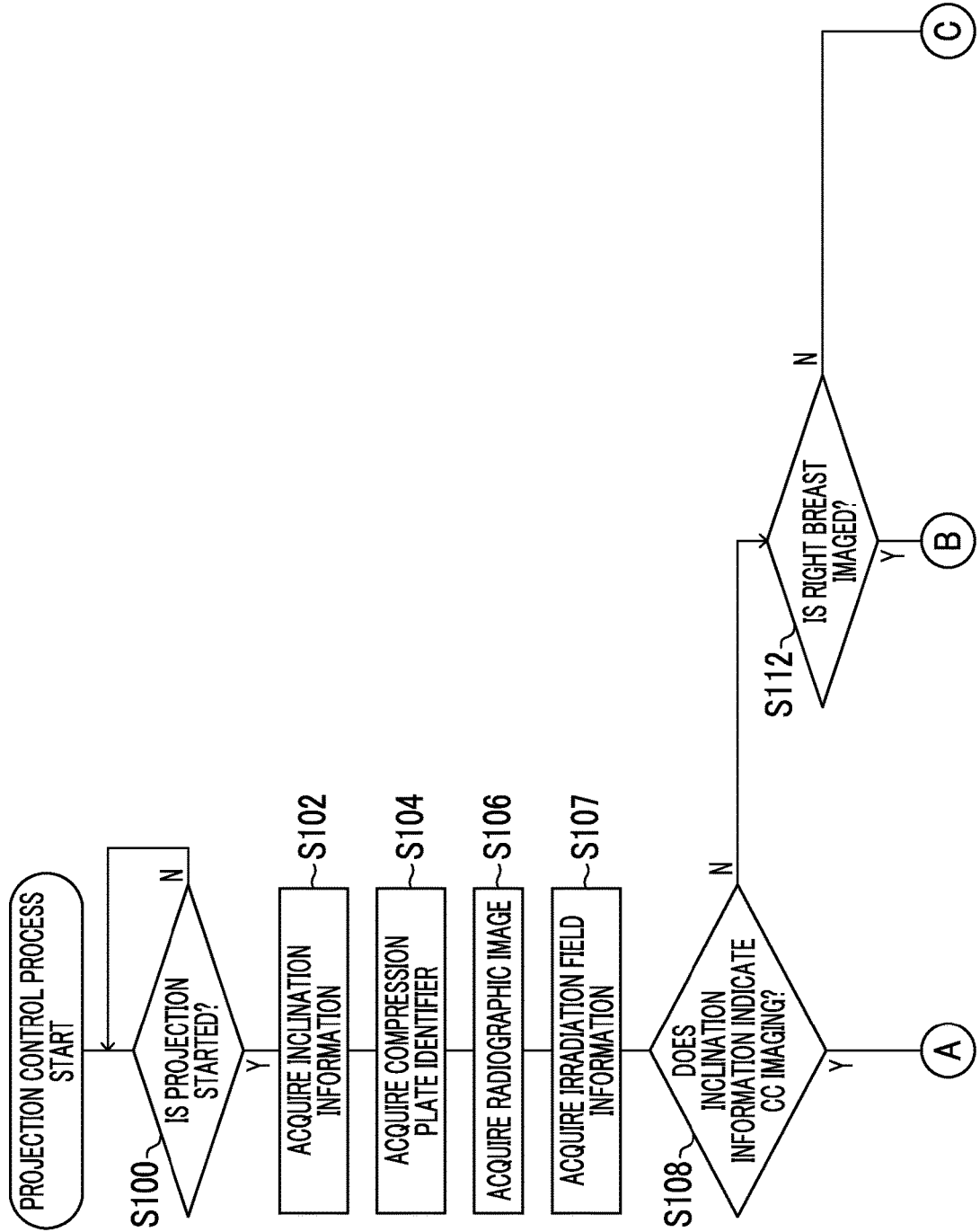
FIGS. 9A and 9B are flowcharts illustrating an example of the flow of a projection control process according to a second embodiment.
Figure 9B:
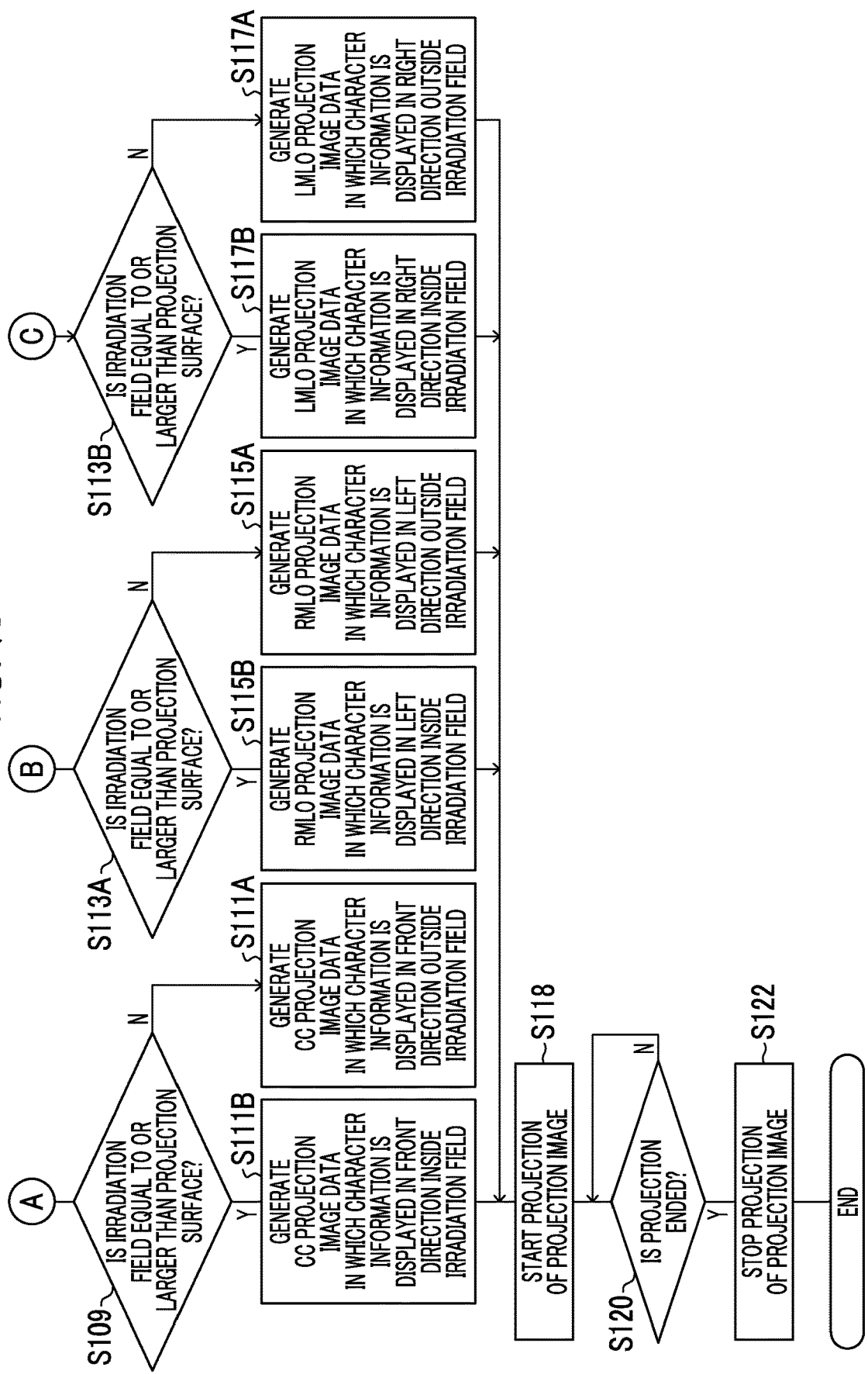

On the other hand, since this embodiment differs from the first embodiment in the projection control process performed in the console 12, the projection control process according to this embodiment will be described. FIGS. 9A and 9B are flowcharts illustrating an example of the flow of the projection control process performed in the console 12 according to this embodiment.

As illustrated in FIGS. 9A and 9B, the projection control process according to this embodiment differs from the projection control process (see FIG. 6) according to the first embodiment in that it comprises a process in Step S107 between Steps S106 and S108. Further, the projection control process according to this embodiment differs from the projection control process according to the first embodiment in that it comprises processes in Steps S109, S111A, and S111B instead of the process in Step S110, comprises processes in Steps S113A, S115A, and S115B instead of the process in Step S114, and comprises processing in Steps S113B, S117A, and S117B instead of the process in Step S110.

As illustrated in FIGS. 9A and 9B, in Step S107, the control unit 62 according to this embodiment acquires irradiation field information indicating the size and position of the irradiation field 102. In addition, for example, in this embodiment, the irradiation field information is included in the imaging menu, and the control unit 62 acquires the irradiation field information from the imaging menu. Further, a method for acquiring the irradiation field information in the control unit 62 is not particularly limited. For example, as described above, in a case in which the size of the irradiation field 102 is determined according to the type of the compression plate 40, such as the compression plate 40A and the compression plate 40B, and the position of the irradiation field 102 with respect to the projection surface 45 is determined according to the type of imaging, such as the CC imaging, the compression plate identifier, the type of imaging, and the irradiation field information may be stored in the storage unit 52 or the like so as to be associated with each other, and the control unit 62 may acquire the irradiation field information corresponding to the type of imaging designated by the imaging menu and the compression plate identifier acquired in Step S104 from the storage unit 52 or the like.

Further, as illustrated in FIGS. 9A and 9B, in a case in which the CC imaging is performed, the determination result in Step S108 is "Yes", and then the process proceeds to Step S109. In Step S109, the control unit 62 determines whether or not the size of the irradiation field 102 is equal to or larger than the size of the projection surface 45.

In a case in which the size of the irradiation field 102 is not equal to or larger than the size of the projection surface 45, in other words, in a case in which the size of the irradiation field 102 is smaller than the size of the projection surface 45, the determination result in Step S109 is "No", and the process proceeds to Step S111A.

In Step S111A, the control unit 62 generates CC projection image data which includes the skin line and in which the direction of the character information displayed in the region 104 outside the irradiation field is the front direction and then proceeds to Step S118. That is, in Step S111A, the control unit 62 generates the projection image P to be projected onto the projection surface 45 of the compression plate 40A. The projector 48 projects the projection image P indicated by the CC projection image data generated by the process in this step such that the state illustrated in FIG. 7A is displayed on the projection surface 45 of the compression plate 40A. In addition, a method for generating the CC projection image data in the control unit 62 is not particularly limited. For example, first, the control unit 62 according to this embodiment generates a skin line image which indicates the skin line indicating the shape of the breast from the radiographic image acquired in Step S106, similarly to the control unit 62 according to the first embodiment. In addition, the control unit 62 combines the image indicating the character information items $74_1$, $74_2$, and $74_3$ in the region 104 outside the irradiation field and the skin line image in a state in which the characters are displayed in the front direction to generate CC projection image data indicating the projection image P to be projected onto the projection surface 45 of the compression plate 40A.

On the other hand, in a case in which the size of the irradiation field 102 is equal to or larger than the size of the projection surface 45 in Step S109, the determination result in Step S109 is "Yes", and the process proceeds to Step S111B.

In Step S111B, the control unit 62 generates CC projection image data which includes the skin line and in which the direction of the character information displayed in the irradiation field 102 is the front direction and then proceeds to Step S118. That is, in Step S111B, the control unit 62 generates the projection image P to be projected onto the projection surface 45 of the compression plate 40B. The projector 48 projects the projection image P indicated by the CC projection image data generated by the process in this step such that the state illustrated in FIG. 8A is displayed on the projection surface 45 of the compression plate 40B. In addition, a method for generating the CC projection image data in the control unit 62 is not particularly limited. For example, first, the control unit 62 according to this embodiment generates a skin line image which indicates the skin line indicating the shape of the breast from the radiographic image acquired in Step S106, similarly to the control unit 62 according to the first embodiment. Further, the control unit 62 combines the image indicating the character information items $74_1$, $74_2$, and $74_3$ at the positions opposite to the chest wall and the skin line image in a state in which the characters are displayed in the front direction to generate CC projection image data indicating the projection image P to be projected onto the projection surface 45 of the compression plate 40B.

Furthermore, as illustrated in FIGS. 9A and 9B, in a case in which the right breast is imaged in the MLO imaging, the determination result in Step S112 is "Yes", the process proceeds to Step S113A. In Step S113A, the control unit 62 determines whether or not the size of the irradiation field 102 is equal to or larger than the size of the projection surface 45.

In a case in which the size of the irradiation field 102 is not equal to or larger than the size of the projection surface 45, in other words, in a case in which the size of the irradiation field 102 is smaller than the size of the projection surface 45, the determination result in Step S113A is "No", and the process proceeds to Step S115A.

In Step S115A, the control unit 62 generates RMLO projection image data which includes the skin line and in which the direction of the character information displayed in the region 104 outside the irradiation field is the left direction and then proceeds to Step S118. That is, in Step S115A, the control unit 62 generates the projection image P to be projected onto the projection surface 45 of the compression plate 40A. The projector 48 projects the projection image P indicated by the RMLO projection image data generated by the process in this step such that the state illustrated in FIG. 7B is displayed on the projection surface 45 of the compression plate 40A. In addition, a method for generating the RMLO projection image data in the control unit 62 is not particularly limited. For example, first, the control unit 62 according to this embodiment generates a skin line image which indicates the skin line indicating the shape of the breast from the radiographic image acquired in Step S106, similarly to the control unit 62 according to the first embodiment. Further, the control unit 62 combines the image indicating the character information items $74_1$, $74_2$, and $74_3$ in the region 104 outside the irradiation field and the skin line image in a state in which the characters are displayed in the left direction to generate RMLO projection image data indicating the projection image P to be projected onto the projection surface 45 of the compression plate 40A.

On the other hand, in a case in which the size of the irradiation field 102 is equal to or larger than the size of the projection surface 45 in Step S113A, the determination result in Step S113A is "Yes", and the process proceeds to Step S115B.

In Step S115B, the control unit 62 generates RMLO projection image data which includes the skin line and in which the direction of the character information displayed in the irradiation field 102 is the left direction and then proceeds to Step S118. That is, in Step S115B, the control unit 62 generates the projection image P to be projected onto the projection surface 45 of the compression plate 40B. The projector 48 projects the projection image P indicated by the RMLO projection image data generated by the process in this step such that the state illustrated in FIG. 8B is displayed on the projection surface 45 of the compression plate 40B. In addition, a method for generating the RMLO projection image data in the control unit 62 is not particularly limited. For example, first, the control unit 62 according to this embodiment generates a skin line image which indicates the skin line indicating the shape of the breast from the radiographic image acquired in Step S106, similarly to the control unit 62 according to the first embodiment. Further, the control unit 62 combines the image indicating the character information items $74_1$, $74_2$, and $74_3$ at the positions opposite to the chest wall and the skin line image in a state in which the characters are displayed in the left direction to generate RMLO projection image data indicating the projection image P to be projected onto the projection surface 45 of the compression plate 40B.

Furthermore, as illustrated in FIGS. 9A and 9B, in a case in which the left breast is imaged in the MLO imaging, the determination result in Step S112 is "No", and the process proceeds to Step S113B. In Step S113B, the control unit 62 determines whether or not the size of the irradiation field 102 is equal to or larger than the size of the projection surface 45.

In a case in which the size of the irradiation field 102 is not equal to or larger than the size of the projection surface 45, in other words, in a case in which the size of the irradiation field 102 is smaller than the size of the projection surface 45, the determination result in Step S113B is "No", and the process proceeds to Step S117A.

In Step S117A, the control unit 62 generates LMLO projection image data which includes the skin line and in which the direction of the character information displayed in the region 104 outside the irradiation field is the right direction and then proceeds to Step S118. That is, in Step S117A, the control unit 62 generates the projection image P to be projected onto the projection surface 45 of the compression plate 40A. The projector 48 projects the projection image P indicated by the LMLO projection image data generated by the process in this step such that the state illustrated in FIG. 7C is displayed on the projection surface 45 of the compression plate 40A. In addition, a method for generating the LMLO projection image data in the control unit 62 is not particularly limited. For example, first, the control unit 62 according to this embodiment generates a skin line image which indicates the skin line indicating the shape of the breast from the radiographic image acquired in Step S106, similarly to the control unit 62 according to the first embodiment. Further, the control unit 62 combines the image indicating the character information items $74_1$, $74_2$, and $74_3$ in the region 104 outside the irradiation field and the skin line image in a state in which the characters are displayed in the right direction to generate LMLO projection image data indicating the projection image P to be projected onto the projection surface 45 of the compression plate 40A.

On the other hand, in a case in which the size of the irradiation field 102 is equal to or larger than the size of the projection surface 45 in Step S113B, the determination result in Step S113B is "Yes", and the process proceeds to Step S117B.

In Step S117B, the control unit 62 generates LMLO projection image data which includes the skin line and in which the direction of the character information displayed in the irradiation field 102 is the right direction and then proceeds to Step S118. That is, in Step S117B, the control unit 62 generates the projection image P to be projected onto the projection surface 45 of the compression plate 40B. The projector 48 projects the projection image P indicated by the LMLO projection image data generated by the process in this step such that the state illustrated in FIG. 8C is displayed on the projection surface 45 of the compression plate 40B. In addition, a method for generating the LMLO projection image data in the control unit 62 is not particularly limited. For example, first, the control unit 62 according to this embodiment generates a skin line image which indicates the skin line indicating the shape of the breast from the radiographic image acquired in Step S106, similarly to the control unit 62 according to the first embodiment. Further, the control unit 62 combines the image indicating the character information items $74_1$, $74_2$, and $74_3$ at the positions opposite to the chest wall and the skin line image in a state in which the characters are displayed in the right direction to generate LMLO projection image data indicating the projection image P to be projected onto the projection surface 45 of the compression plate 40B.

As described above, the console 12 according to this embodiment performs control such that the display positions of the character information items $74_1$ to $74_3$ displayed on the projection surface 45 of the compression plate 40 by the projection image P differ depending on the size and position of the irradiation field 102 with respect to the projection surface 45 of the compression plate 40. In the console 12 according to this embodiment, in a case in which the size of the irradiation field 102 is smaller than the size of the projection surface 45, the character information items $74_1$ to $74_3$ are displayed in the region 104 outside the irradiation field. Therefore, the user can recognize the position of the region 104 outside the irradiation field and furthermore the position of the irradiation field 102 on the basis of the position where the character information items $74_1$ to $74_3$ are displayed. In addition, similarly to the console 12 according to the first embodiment, the console 12 according to this embodiment performs control such that the direction of the character information displayed on the projection surface 45 of the compression plate 40 by the projection image P differs depending on the inclination of the imaging surface 30A of the imaging table 30 in each imaging operation. Therefore, according to the console 12 of this embodiment, it is possible to reduce the burden on the user who positions the breast.

As described above, the console 12 according to each of the above-described embodiments comprises the CPU 50A as at least one processor. The CPU 50A acquires the inclination information indicating the inclination of the imaging surface 30A of the imaging table 30 in the mammography apparatus 10 which irradiates the breast in the compressed state between the imaging surface 30A of the imaging table 30 and the compression plate 40 with the radiation R from the radiation source 37R to capture a radiographic image. In addition, the CPU 50A performs control to adjust the information displayed on the projection surface 45 of the compression plate 40 by the projection of the projection image by the projector 48 according to the inclination indicated by the inclination information.

The position where the user stands to position the breast is determined according to the inclination of the imaging surface 30A of the imaging table 30. Since the console 12 according to each of the above-described embodiments adjusts the information displayed on the projection surface 45 of the compression plate 40 according to the inclination of the imaging surface 30A of the imaging table 30, the information is adjusted according to the position where the user stands. Therefore, according to the console 12 of each of the above-described embodiments, the information is displayed such that it is easy for the user to see the information. Therefore, according to the console 12 of each of the above-described embodiments, it is possible to reduce the burden on the user who positions the breast.

In each of the above-described embodiments, the aspect in which the projection of the projection image P by the projector 48 is started in a case in which the user inputs a projection start instruction has been described. However, the timing when the projection of the projection image P is started is not limited to this aspect. For example, the projection may be started at the timing when an imaging menu is instructed from the console 12 to the mammography apparatus 10.

Further, the configuration for projecting the projection image P in the mammography apparatus 10 is not limited and is not limited to the aspect using the projector 48 described in each of the above-described embodiments. Further, in a case in which the projector 48 is applied, the configuration of the projector 48 is not limited. For example, in each of the above-described embodiments, the aspect in which the projection image P projected from the projector 48 is directly projected onto the projection surface 45 has been described. However, the projection image P may be reflected from a mirror or the like to be projected onto the projection surface 45. In this case, the direction in which the projection image P is projected can be adjusted by the mirror or the like. Furthermore, for example, a shutter or the like that blocks the projection light may be provided in front of the projection unit 48B of the projector 48. In this case, the shutter may be opened or closed to control the projection of the projection image P onto the projection surface 45. Specifically, in a case in which the projection of the projection image P is started, control is performed such that the shutter is opened to transmit the projection light. On the other hand, in a case in which the projection of the projection image P is ended, control is performed such that the shutter is closed to block the projection light.

Further, in each of the above-described embodiments, the power supply unit 48A of the projector 48 may be turned on before the projection image P is projected, and the specific timing when the power supply unit 48A is turned on is not limited, which is not described above. For example, the power supply unit 48A may be turned on immediately after the projection control process is started in the console 12 or immediately before the projection image P is projected.

Further, in each of the above-described embodiments, the aspect in which the skin line is applied as the information indicating at least one of the shape or position of the breast has been described. However, the information indicating at least one of the shape or position of the breast is not limited to the skin line. The information indicating at least one of the shape or position of the breast may be any information for guiding the user to position the breast compressed by the compression plate 40. For example, information indicating the position of the nipple may be used as the information indicating at least one of the shape or position of the breast. In addition, the radiographic image of the breast may be used as the information indicating at least one of the shape or position of the breast.

Further, the character information displayed on the projection surface 45 of the compression plate 40 is not limited to the character information items $74_1$ to $74_3$. It is preferable that the character information includes at least one of the compression pressure of the compression plate 40 against the breast in the past imaging and the current imaging, the thickness of the compressed breast, or information indicating the degree of inclination as in the character information items $74_1$ to $74_3$ according to each of the above-described embodiments.

In a case in which the compression pressure in the current imaging is used as the character information, for example, a compression pressure detection sensor that is provided in the compression unit 36 may detect the compression pressure which is the pressure related to the compression plate 40, and the control unit 62 may acquire the detected compression pressure and apply the acquired compression pressure to the character information. In this case, examples of the compression pressure detection sensor include a semiconductor-type pressure sensor, a capacitance-type pressure sensor, and a strain gauge such as a load cell. Further, the compression force of the compression plate 40 against the entire breast or compression pressure which is compression force per unit area may be applied as the compression pressure. Furthermore, in a case in which the thickness of the breast in the current imaging is used as the character information, for example, the amount of movement of the compression plate 40 by the compression plate driving unit 42 may be acquired, and the control unit 62 may derive the distance between the compression plate 40 and the imaging surface 30A of the imaging table 30 as the thickness of the breast on the basis of the amount of movement of the compression plate 40 and apply the distance to the character information.

In addition, in each of the above-described embodiments, the aspect in which the information indicating the type of imaging is applied as an example of the information indicating the degree of inclination has been described. However, the information indicating the degree of inclination is not limited to this aspect. For example, the angle at which the imaging surface 30A of the imaging table 30 is inclined, the rotation angle of the arm portion 32, or the like may be applied as the information indicating the degree of inclination. Further, the character information may be, for example, information related to the current imaging, such as an imaging date and time, information related to the subject, such as the name of the subject, and information related to the radiographer.

Further, in each of the above-described embodiments, the aspect in which the size of the projection image P is equal to or less than the size of the projection surface 45 has been described. However, the size of the projection image P may be equal to or greater than the size of the projection surface 45 of the compression plate 40. That is, the projection image P may be projected onto the imaging surface 30A of the imaging table 30. Furthermore, the projection image P may be projected only on the imaging table 30. Further, for example, the projection image P may be displayed on the wall portion 41B of the compression plate 40. In addition, in a case in which the projection image P is displayed on the wall portion 41B of the compression plate 40, the wall portion 41B on which the projection image P is displayed may differ depending on the inclination of the imaging surface 30A of the imaging table 30. For example, in the compression plate 40 illustrated in FIG. 2C, since the compression portion 41 has a rectangular shape, the wall portions 41B are provided on four sides of the rectangular shape. In this case, the control unit 62 may perform control to display the projection image P on the wall portion 41B, which is easy for the user who positions the breast to see, at a position that is determined according to the inclination of the imaging surface 30A of the imaging table 30.

Further, in each of the above-described embodiments, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the acquisition unit 60 and the control unit 62. Specifically, a device other than the console 12 may comprise a processor and the projection control program 51, and the processor may execute the projection control program 51 to function as the acquisition unit 60 and the control unit 62.

Further, in each of the above-described embodiments, for example, the following various processors can be used as the hardware structure of processing units performing various processes such as the acquisition unit 60 and the control unit 62. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the projection control program 51 is stored (installed) in the ROM 50B in advance has been described. However, the present disclosure is not limited thereto. The projection control program 51 may be recorded on a recording medium, such as a compact disc read only memory (CD-ROM), a digital versatile disc read only memory (DVD-ROM), or a universal serial bus (USB) memory, and then provided. In addition, the projection control program 51 may be downloaded from an external device through a network.

What is claimed is:

1. A control device comprising:
   at least one processor,
   wherein the processor is configured to
   acquire inclination information indicating an inclination of an imaging surface of an imaging table in a mammography apparatus that irradiates a breast in a compressed state between the imaging surface of the imaging table and a compression member with radiation from a radiation source to capture a radiographic image and
   perform control to adjust information, which is displayed on a projection surface of the compression member by projection of a projection image by an image projection unit, according to the inclination indicated by the inclination information.

2. The control device according to claim 1,
   wherein the processor is configured to
   perform control to adjust a direction in which the information is displayed to a direction corresponding to the inclination.

3. The control device according to claim 1,
   wherein the processor is configured to
   perform control to switch the direction, in which the information is displayed, between a case in which the imaging surface of the imaging table is inclined with respect to the subject pertaining to the breast and a case in which the imaging surface is not inclined with respect to the subject.

4. The control device according to claim 1,
   wherein the processor is configured to
   not to perform the control regardless of the inclination in a case in which the information is information indicating at least one of a shape or a position of the breast.

5. The control device according to claim 1,
   wherein, in a case in which the information includes character information, the processor is configured to perform control to adjust a display position of the character information to a position corresponding to the inclination.

6. The control device according to claim 1,
   wherein, in a case in which a size of an irradiation field of the radiation emitted from the radiation source is smaller than a size of the projection surface and the information is character information, the processor is configured to perform control to adjust a display position of the character information to a position outside the irradiation field.

7. The control device according to claim 5,
   wherein the character information includes characters indicating at least one of a compression pressure of the compression member against the breast in past imaging and current imaging, a thickness of the compressed breast, or information indicating a degree of the inclination.

8. The control device according to claim 1,
   wherein, in a case in which a size of an irradiation field of the radiation emitted from the radiation source is smaller than a size of the projection surface and the information is information indicating at least one of a shape or a position of the breast in the compressed state, the processor is configured to perform control to adjust a display position of the information to a position inside the irradiation field.

9. The control device according to claim 1,
   wherein, in a case in which a size of an irradiation field of the radiation emitted from the radiation source is equal to or larger than a size of the projection surface, the processor is configured to perform control to adjust a display position of the information to the same position regardless of the inclination.

10. A control device comprising:
    at least one processor,
    wherein the processor is configured to
    perform control such that a direction of information displayed on a projection surface of a compression member by a projection image projected by an image projection unit is different between a case in which a mammography apparatus performs cranio-caudal (CC) imaging in which a radiation source and an imaging table are disposed in a cranio-caudal direction of a subject and a radiographic image of a breast of the subject compressed by the compression member is captured and a case in which the mammography apparatus performs mediolateral oblique (MLO) imaging in which the radiation source and the imaging table are inclined with respect to the subject and a radiographic image of the breast compressed by the compression member is captured.

11. The control device according to claim 10,
    wherein the processor is configured to perform the control on character information including at least one of a compression pressure of the compression member against the breast in past imaging and current imaging, a thickness of the compressed breast, or information indicating a degree of inclination of the radiation source and the imaging table with respect to the subject and performs control such that information indicating a shape of the breast is displayed in the same direction in a case in which the CC imaging is performed and in a case in which the MLO imaging is performed.

12. A control device comprising:
    at least one processor,
    wherein the processor is configured to
    control an image projection unit which projects a projection image onto a projection surface of a compression member in a mammography apparatus that irradiates a breast compressed by the compression member with radiation from a radiation source to capture a radiographic image such that, in a case in which a size of an irradiation field of the radiation emitted from the radiation source is equal to or larger than a size of an image displayed on the projection surface by the projection image, character information including characters indicating at least one of a compression pressure of the compression member against the breast in past imaging and current imaging, a thickness of the compressed breast, or information indicating a degree of inclination of a support portion that supports the radiation source with respect to a subject pertaining to the breast is displayed inside the irradiation field and that, in a case in which the size of the irradiation field is smaller than the size of the image displayed on the projection surface by the projection image, the character information is displayed outside the irradiation field.

13. A non-transitory computer-readable storage medium storing a control program that causes a computer to perform a process comprising:
  acquiring inclination information indicating an inclination of an imaging surface of an imaging table in a mammography apparatus that irradiates a breast in a compressed state between the imaging surface of the imaging table and a compression member with radiation from a radiation source to capture a radiographic image; and
  performing control to adjust information, which is displayed on a projection surface of the compression member by projection of a projection image by an image projection unit, according to the inclination indicated by the inclination information.

14. A non-transitory computer-readable storage medium storing a control program that causes a computer to perform a process comprising:
  performing control such that a direction of information displayed on a projection surface of a compression member by a projection image projected by an image projection unit is different between a case in which a mammography apparatus performs cranio-caudal (CC) imaging in which a radiation source and an imaging table are disposed in a cranio-caudal direction of a subject and a radiographic image of a breast of the subject compressed by the compression member is captured and a case in which the mammography apparatus performs mediolateral oblique (MLO) imaging in which the radiation source and the imaging table are inclined with respect to the subject and a radiographic image of the breast compressed by the compression member is captured.

15. A non-transitory computer-readable storage medium storing a control program that causes a computer to perform a process comprising:
  controlling an image projection unit which projects a projection image onto a projection surface of a compression member in a mammography apparatus that irradiates a breast compressed by the compression member with radiation from a radiation source to capture a radiographic image such that, in a case in which a size of an irradiation field of the radiation emitted from the radiation source is equal to or larger than a size of an image displayed on the projection surface by the projection image, character information including characters indicating at least one of a compression pressure of the compression member against the breast in past imaging and current imaging, a thickness of the compressed breast, or information indicating a degree of inclination of a support portion that supports the radiation source with respect to a subject pertaining to the breast is displayed inside the irradiation field and that, in a case in which the size of the irradiation field is smaller than the size of the image displayed on the projection surface by the projection image, the character information is displayed outside the irradiation field.

* * * * *